US012336999B2

(12) United States Patent
Ferdous et al.

(10) Patent No.: US 12,336,999 B2
(45) Date of Patent: Jun. 24, 2025

(54) MODIFIED RELEASE FORMULATIONS OF 2-[3-[4-AMINO-3-(2-FLUORO-4-PHENOXY-PHENYL) PYRAZOLO[3,4-D] PYRIMIDIN-1-YL]PIPERIDINE-1-CARBONYL]-4-METHYL-4-[4-(OXETAN-3-YL) PIPERAZIN-1-YL]PENT-2-ENENITRILE

(71) Applicant: Principia Biopharma Inc., Bridgewater, NJ (US)

(72) Inventors: Abu J. Ferdous, Belmont, CA (US); Mohammad R. Masjedizadeh, San Jose, CA (US); Wu Lin, Nottingham (GB)

(73) Assignee: Principia Biopharma Inc., Bridgewater, NJ (US)

( * ) Notice: Subject to any disclaimer, the term of this patent is extended or adjusted under 35 U.S.C. 154(b) by 0 days.

(21) Appl. No.: 18/526,225

(22) Filed: Dec. 1, 2023

(65) Prior Publication Data

US 2024/0207275 A1 Jun. 27, 2024

Related U.S. Application Data

(60) Division of application No. 17/082,747, filed on Oct. 28, 2020, now Pat. No. 11,872,229, which is a continuation of application No. 16/312,258, filed as application No. PCT/US2017/040075 on Jun. 29, 2017, now abandoned.

(60) Provisional application No. 62/356,345, filed on Jun. 29, 2016.

(51) Int. Cl.
| | |
|---|---|
| A61K 31/519 | (2006.01) |
| A61K 9/20 | (2006.01) |
| A61K 9/28 | (2006.01) |
| A61K 9/50 | (2006.01) |

(52) U.S. Cl.
CPC .......... *A61K 31/519* (2013.01); *A61K 9/2018* (2013.01); *A61K 9/2846* (2013.01); *A61K 9/2866* (2013.01); *A61K 9/2886* (2013.01); *A61K 9/5026* (2013.01); *A61K 9/5047* (2013.01); *A61K 9/5073* (2013.01)

(58) Field of Classification Search
None
See application file for complete search history.

(56) References Cited

U.S. PATENT DOCUMENTS

| | | |
|---|---|---|
| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,331,555 B1 | 12/2001 | Hirth et al. |
| 6,410,486 B2 | 6/2002 | Wetterich et al. |
| 6,596,746 B1 | 7/2003 | Das et al. |
| 6,660,744 B1 | 12/2003 | Hirst et al. |
| 7,217,682 B2 | 5/2007 | Mori |
| 7,514,444 B2 | 4/2009 | Honigberg et al. |
| 7,700,648 B2 | 4/2010 | Mori |
| 8,673,925 B1 | 3/2014 | Goldstein |
| 8,759,358 B1 | 6/2014 | Goldstein |
| 8,828,426 B2 | 9/2014 | Shah et al. |
| 8,940,744 B2 | 1/2015 | Owens et al. |
| 8,946,241 B2 | 2/2015 | Goldstein |
| 8,957,080 B2 | 2/2015 | Goldstein et al. |
| 8,962,635 B2 | 2/2015 | Goldstein |
| 8,962,831 B2 | 2/2015 | Goldstein |
| 9,090,621 B2 | 7/2015 | Goldstein |
| 9,266,895 B2 | 2/2016 | Owens et al. |
| 9,376,438 B2 | 6/2016 | Goldstein et al. |
| 9,572,811 B2 | 2/2017 | Babler et al. |
| 9,688,676 B2 | 6/2017 | Owens |
| 9,994,576 B2 | 6/2018 | Owens et al. |
| 10,092,569 B2 | 10/2018 | Masjedizadeh et al. |
| 10,456,403 B2 | 10/2019 | Masjedizadeh et al. |
| 10,485,797 B2 | 11/2019 | Gourlay |
| 10,533,013 B2 | 1/2020 | Owens et al. |
| 10,828,307 B2 | 11/2020 | Masjedizadeh et al. |
| 11,040,980 B2 | 6/2021 | Owens et al. |
| 11,369,613 B2 | 6/2022 | Masjedizadeh et al. |
| 2003/0153752 A1 | 8/2003 | Hirst et al. |
| 2003/0187001 A1 | 10/2003 | Calderwood et al. |
| 2004/0006083 A1 | 1/2004 | Hirst et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2006/0079494 A1 | 4/2006 | Santi et al. |
| 2006/0275376 A1 | 12/2006 | Guimberteau et al. |

(Continued)

FOREIGN PATENT DOCUMENTS

| | | |
|---|---|---|
| CA | 2890111 A1 | 5/2014 |
| CN | 1274280 A | 11/2000 |

(Continued)

OTHER PUBLICATIONS

Structure-Based Search Results (May 9, 2011, 8:23 PM), SciFinder.

(Continued)

Primary Examiner — Jake M Vu
(74) Attorney, Agent, or Firm — McNeill PLLC

(57) ABSTRACT

Modified release formulations, such as solid oral dosage forms comprising a core composition comprising Compound (I) and/or a pharmaceutically acceptable salt thereof; a sub-coating layer coating the core composition, said sub-coating layer comprising a polyvinyl alcohol and/or a hydroxypropyl methyl cellulose; and an enteric coating layer encapsulating the sub-coating layer and the core composition, said enteric coating layer comprising at least one polymer selected from an acrylic/methacrylic/ethacrylic acid homopolymer and copolymers thereof, a cellulose derivative, and a polyvinylpyrrolidone, and methods of administration of a Bruton's tyrosine kinase (BTK) inhibitor using said formulations.

20 Claims, 3 Drawing Sheets

(56) References Cited

U.S. PATENT DOCUMENTS

| | | |
|---|---|---|
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0076921 A1 | 3/2008 | Honigberg et al. |
| 2008/0146643 A1 | 6/2008 | Billen et al. |
| 2008/0176865 A1 | 7/2008 | Billen et al. |
| 2008/0260818 A1 | 10/2008 | Penhasi et al. |
| 2009/0215750 A1 | 8/2009 | Bamberg et al. |
| 2009/0215788 A1 | 8/2009 | Elworthy et al. |
| 2009/0306396 A1 | 12/2009 | Toyoshima et al. |
| 2010/0113520 A1 | 5/2010 | Miller |
| 2010/0144705 A1 | 6/2010 | Miller |
| 2010/0152143 A1 | 6/2010 | Priebe et al. |
| 2010/0254905 A1 | 10/2010 | Honigberg et al. |
| 2010/0280035 A1 | 11/2010 | Becker et al. |
| 2011/0021518 A1 | 1/2011 | Magnuson et al. |
| 2011/0086866 A1 | 4/2011 | Chen et al. |
| 2012/0028981 A1 | 2/2012 | Miller |
| 2012/0071497 A1 | 3/2012 | Buggy et al. |
| 2012/0149687 A1 | 6/2012 | Lee et al. |
| 2013/0079327 A1 | 3/2013 | Yamamoto et al. |
| 2013/0197014 A1 | 8/2013 | Chen et al. |
| 2014/0094459 A1 | 4/2014 | Goldstein et al. |
| 2014/0142099 A1 | 5/2014 | Owens |
| 2014/0221398 A1 | 8/2014 | Goldstein et al. |
| 2014/0256734 A1 | 9/2014 | Lawson et al. |
| 2014/0303190 A1 | 10/2014 | Goldstein |
| 2014/0364410 A1 | 12/2014 | Owens et al. |
| 2015/0140085 A1 | 5/2015 | Goldstein |
| 2015/0209432 A1 | 7/2015 | Konda et al. |
| 2015/0328310 A1 | 11/2015 | Allen et al. |
| 2015/0353557 A1 | 12/2015 | Goldstein et al. |
| 2015/0353562 A1 | 12/2015 | Goldstein |
| 2016/0045503 A1 | 2/2016 | Goldstein et al. |
| 2016/0113913 A1 | 4/2016 | Murakawa et al. |
| 2016/0257686 A1 | 9/2016 | Owens |
| 2016/0376277 A1 | 12/2016 | Desai et al. |
| 2017/0065591 A1 | 3/2017 | Masjedizadeh et al. |
| 2018/0015088 A1 | 1/2018 | Nunn et al. |
| 2018/0162861 A1 | 6/2018 | Goldstein et al. |
| 2018/0193274 A1 | 7/2018 | Nunn et al. |
| 2018/0305350 A1 | 10/2018 | Goldstein et al. |
| 2018/0327413 A1 | 11/2018 | Owens et al. |
| 2019/0231784 A1 | 8/2019 | Ferdous et al. |
| 2019/0345159 A1 | 11/2019 | Goldstein et al. |
| 2020/0038405 A1 | 2/2020 | Masjedizadeh et al. |
| 2020/0101059 A1 | 4/2020 | Gourlay |
| 2020/0190092 A1 | 6/2020 | Owens et al. |
| 2021/0106584 A1 | 4/2021 | Gourlay et al. |
| 2021/0221818 A1 | 7/2021 | Phiasivongsa et al. |

FOREIGN PATENT DOCUMENTS

| | | | |
|---|---|---|---|
| CN | 1681483 A | 10/2005 | |
| CN | 1874761 A | 12/2006 | |
| CN | 101287452 A | 10/2008 | |
| CN | 101610676 A | 12/2009 | |
| CN | 101730699 A | 6/2010 | |
| CN | 101880243 A | 11/2010 | |
| CN | 102159214 A | 8/2011 | |
| CN | 101610676 B | 3/2013 | |
| CN | 103096716 A | 5/2013 | |
| CN | 101805341 A | 7/2013 | |
| CN | 101805341 B | 7/2013 | |
| CN | 103534258 A | 1/2014 | |
| CN | 104640861 A | 5/2015 | |
| CN | 104736178 A | 6/2015 | |
| CN | 104822681 A | 8/2015 | |
| CN | 103096716 B | 3/2016 | |
| CN | 105753863 A | 7/2016 | |
| CN | 103534258 B | 9/2016 | |
| CN | 106456652 A | 2/2017 | |
| CN | 110483521 A | 11/2019 | |
| CN | 106456652 B | 9/2020 | |
| EP | 0461546 A2 | 12/1991 | |
| EP | 0493767 A2 | 7/1992 | |
| EP | 0461546 A3 | 3/1993 | |
| EP | 0493767 A3 | 3/1993 | |
| EP | 0908457 A1 | 4/1999 | |
| EP | 2443929 A1 | 4/2012 | |
| EP | 2578585 A1 | 4/2013 | |
| EP | 2578585 B1 | 7/2016 | |
| FR | 2535721 A1 | 5/1984 | |
| GB | 2447933 A | 10/2008 | |
| JP | 5663950 A | 5/1981 | |
| JP | 021450 | 1/1990 | |
| JP | 04177244 | 6/1992 | |
| JP | 2005239657 A | 9/2005 | |
| JP | 2010504324 A | 2/2010 | |
| JP | 2010235628 A | 10/2010 | |
| JP | 2014513729 A | 6/2014 | |
| JP | 2014517838 A | 7/2014 | |
| JP | 2015522653 A | 8/2015 | |
| JP | 2016503063 A | 2/2016 | |
| JP | 6203848 B2 | 9/2017 | |
| WO | 9524190 A2 | 9/1995 | |
| WO | 9531432 A1 | 11/1995 | |
| WO | 9841499 A1 | 9/1998 | |
| WO | 9914216 A1 | 3/1999 | |
| WO | 9918938 A1 | 4/1999 | |
| WO | 0172751 A1 | 10/2001 | |
| WO | 02066463 A1 | 8/2002 | |
| WO | 03037890 A2 | 5/2003 | |
| WO | 03050080 A1 | 6/2003 | |
| WO | 03068157 A2 | 8/2003 | |
| WO | 03082807 A2 | 10/2003 | |
| WO | 2004016259 A1 | 2/2004 | |
| WO | 2004074283 A1 | 9/2004 | |
| WO | 2005020929 A2 | 3/2005 | |
| WO | 2005023773 A1 | 3/2005 | |
| WO | 2005030184 A2 | 4/2005 | |
| WO | 2005085210 A1 | 9/2005 | |
| WO | 2006086634 A2 | 8/2006 | |
| WO | 2006134468 A1 | 12/2006 | |
| WO | 2007043401 A1 | 4/2007 | |
| WO | 2007087068 A2 | 8/2007 | |
| WO | 2007130075 A1 | 11/2007 | |
| WO | 2007142755 A2 | 12/2007 | |
| WO | 2008005954 A2 | 1/2008 | |
| WO | 2008006032 A1 | 1/2008 | |
| WO | 2007087068 A3 | 2/2008 | |
| WO | 2008039218 A2 | 4/2008 | |
| WO | 2008054827 A2 | 5/2008 | |
| WO | 2008061740 A1 | 5/2008 | |
| WO | 2008072053 A2 | 6/2008 | |
| WO | 2008072077 A2 | 6/2008 | |
| WO | 2008116064 A2 | 9/2008 | |
| WO | 2008121742 A2 | 10/2008 | |
| WO | 2009140128 A2 | 11/2009 | |
| WO | 2009143477 A1 | 11/2009 | |
| WO | 2010009342 A1 | 1/2010 | |
| WO | 2010014930 A2 | 2/2010 | |
| WO | 2010065898 A2 | 6/2010 | |
| WO | 2011031896 A2 | 3/2011 | |
| WO | 2011046964 A2 | 4/2011 | |
| WO | 2011060440 A1 | 5/2011 | |
| WO | 2011144585 A1 | 11/2011 | |
| WO | 2011152351 A1 | 12/2011 | |
| WO | 2011153514 A2 | 12/2011 | |
| WO | 2012021444 A1 | 2/2012 | |
| WO | 2012158764 A1 | 11/2012 | |
| WO | 2012158795 A1 | 11/2012 | |
| WO | 2012158810 A1 | 11/2012 | |
| WO | 2012158843 A2 | 11/2012 | |
| WO | 2013003629 A2 | 1/2013 | |
| WO | 2013010136 A1 | 1/2013 | |
| WO | 2013010380 A1 | 1/2013 | |
| WO | 2013010868 A1 | 1/2013 | |
| WO | 2013010869 A1 | 1/2013 | |
| WO | 2013041605 A1 | 3/2013 | |
| WO | 2013059738 A2 | 4/2013 | |
| WO | 2013102059 A1 | 7/2013 | |
| WO | 2013116382 A1 | 8/2013 | |

(56) References Cited

FOREIGN PATENT DOCUMENTS

| | | |
|---|---|---|
| WO | 2013184572 A1 | 12/2013 |
| WO | 2013185082 A2 | 12/2013 |
| WO | 2013191965 A1 | 12/2013 |
| WO | 2014004707 A1 | 1/2014 |
| WO | 2014022569 A1 | 2/2014 |
| WO | 2014039899 A1 | 3/2014 |
| WO | 2014068527 A1 | 5/2014 |
| WO | 2014078578 A1 | 5/2014 |
| WO | 2014164558 A1 | 10/2014 |
| WO | 2014171542 A1 | 10/2014 |
| WO | 2015127310 A1 | 8/2015 |
| WO | 2015132799 A2 | 9/2015 |
| WO | 2016100914 A1 | 6/2016 |
| WO | 2016105531 A1 | 6/2016 |
| WO | 2017041536 A1 | 3/2017 |
| WO | 2017066014 A1 | 4/2017 |
| WO | 2018005849 A1 | 1/2018 |
| WO | 2019208805 A1 | 10/2019 |
| WO | 2021076514 A1 | 4/2021 |
| WO | 2022081512 A1 | 4/2022 |

OTHER PUBLICATIONS

Structure-Based Search Results (May 9, 2011, 8:33 PM), SciFinder.
Structure-Based Search Results (May 9, 2011, 9:06 PM), SciFinder.
Van Beek, N. et al., "Therapy of pemphigus", Hautarzt, Springer Verlag, Berlin, DE, vol. 70, No. 4, pp. 243-253 (Mar. 18, 2019).
Vayne, C., et al., "Pathophysiology and Diagnostic of Drug-Induced Immune Thrombocytopenia," Journal of Clinical Medicine, vol. 9, No. 7, p. 2212 (2020).
Verhe, R., et al., "Preparation of 2,2-Dialkylcyclopropanes Geminally Substituted with Electron-Withdrawing Groups," Synthesis, vol. 7, pp. 530-532 (1978).
Verhe, R., et al., "Synthesis of 1,1-Bis(Hydroxymethyl) Cyclopropanes," Organic Preparations and Procedures International, vol. 13, No. 1, pp. 13-18 (1981).
Verhe, R., et al., "Thermal Lactonization of Brominated Alkylidenemalonates: Synthesis of 2-Buten-4-Olides," Bulletin des Societes Chimiques Belges, vol. 87, No. 3, pp. 215-222 (1978).
Vo, N., et al., "Transformations of Resin-Bound Pyridinium Ylides: I. A Stereoselective Synthesis of 2,2,3-Trisubstituted Cyclopropanecarboxylates," Tetrahedron Letters, vol. 38, No. 46, pp. 7951-7954 (1997).
Von Hundelshausen, P., et al., "Vaccine-Induced Immune Thrombotic Thrombodytopenia (VITT): Targeting Pathomechanisms with Bruton Tyrosine Kinase Inhibitors", Thrombosis and Haemostasis, vol. 121, No. 11, pp. 1395-1399 (2021).
Wang, G., et al., "Substituted 4-amino-1H-pyrazolo[3,4-d]pyrimidines as multi-targeted inhibitors of insulin-like growth factor-I receptor (IGFIR) and members of ErbB-family receptor kinases," Bioorganic Medicinal and Chemistry Letters, vol. 20, pp. 6067-6071 (2010).
Wang, K., et al., "Cyanoacetamide Multicomponent Reaction (I): Parallel Synthesis of Cyanoacetamides," Journal of Combinatorial Chemistry, vol. 11, pp. 920-927 (2009).
WebMD. 10 Ways to Prevent Psoriasis Flare-Ups. Web: (2016).
WebMD. Multiple Sclerosis (MS)-Prevention. Web: < http://www.webmd.com/multiple-sclerosis/tc/multiple-sclerosis-ms-prevention> (2015).
Wells, G., et al., "Structural Studies on Bioactive Compounds. 32.1 Oxidation of Tyrphostin Protein Tyrosine Kinase Inhibitors with Hypervalent Iodine Reagents," Journal of Medicinal Chemistry, vol. 43. pp. 1550-1562 (2000).
WhatisDryEye.com. Dry Eye vs. Conjunctivitis Web: (2016).
Wilding, I., et al., "Targeting of Drugs and Vaccines to the Gut," Pharmacology and Therapeutics, vol. 62, pp. 97-124 (1994).
Wissner, A., et al., "Synthesis and Structure-Activity Relationships of 6,7-Disubstituted 4-Anilinoquinoline-3-carbonitriles. The Design of an Orally Active, IrreversibleInhibitor of the Tyrosine Kinase Activity of the Epidermal Growth Factor Receptor (EGFR) and the Human Epidermal Growth Factor Receptor-2 (HER-2)," Journal of Medicinal Chemistry, vol. 46, pp. 49-63 (2003).
Wong, J.D., "The ruthless player in purpura: immune thrombocytopenia purpura," https://tpech.gov.taipei/mp109181/News_Content.aspx?n=80359412498D4193&sms =D6D8C221F7AECFEE&s=0419C614DFB65D7A, Sep. 4, 2012.
Zhang, F., et al., "Organic base catalyzed carbonyl allylation of methyl trifluoropyruvate with activated alkenes," Tetrahedron Letters, vol. 65, pp. 83-86 (2009).
Zhensu, L., Medicinal Chemistry, Chemical Industry Press, China, Mar. 3, 1981, pp. 435-436.
Zimmerman, H., et al., "The Diverted Di-TT-Methane Rearrangement; Mechanistic and Exploratory Organic Photochemistry," Organic Letters, vol. 4, No. 7, pp. 1155-1158 (2002).
U.S. Appl. No. 63/176,543, filed Apr. 19, 2021, Christopher W. Smith.
"Solubility, Polymorphism, Crystallinity, and Crystal Habit of Acetaminophen and Ibuprofen by Initial Solvent Screening," PharmaTech.com, vol. 30, No. 10, pp. 1-3 (2006).
"Supplement Article", The Authors, British Journal of Haematology, vol. 185, suppl. 1, pp. 3-202 (2019).
2012 ICD-9-CM Diagnosis Code 372.30: Conjunctivitis, unspecified, retrieved Aug. 4, 2016 (1 page).
Abdulahad, W., et al., "Immune regulation and B-cell depletion therapy in patients with primary Sjogren's syndrome," J Autoimmun, 39(1): 103-111 (2012).
Abstract for Neplyuev, V., "Nitration and nitrosation of 1, 1,3,3-tetraacyl-1-propenes" Ukrainskii Khimicheskii Zhurnal (Russian Edition), 49(2):192-194 (1 page) (1983).
Abstract for Neplyuev, V., "Studies of triacylmethanes VII. 1, 1,3,3-Tetraacyl-3-arylazo-1-propenes," Zhurnal Organicheskoi Khimii, 15(3): 563-566 (1 page) (1979).
American Cancer Society. Can Non-Hodgkin's Lymphoma Be Prevented? (2016) Web: (3 pages).
Ansel, H., et al., "Pharmaceutical Dosage Forms and Drug Delivery Systems," Seventh Edition, Lippincott Williams & Wilkins, A Wolters Kluwer Company, Chapters 1-8, pp. 1-243 (1999).
Armesto, D., et al., "Efficient photochemical synthesis of 2-vinylcyclopropanecarbaldehydes, precursors of cyclopropane components present i1 pyrethroids, by using the oxa-di-TT-methane rearrangement," Tetrahedron, 66: 8690-8697 (2010).
Arnold, L., et al., "Pyrrolo[2,3-d]pyrimidines Containing an Extended 5-Substituent as Potent and Selective Inhibitors of Ick I," Bioorg. Med. Chem. Lett., 10:2167-2170 (2000).
Arora, A., et al., "Role of Tyrosine Kinase Inhibitors in Cancer Therapy," J Pharmacol. Exp. Ther., 315(3):971-979 (2005).
Audia, S., et al., "Pathogenesis of immune thrombocytopenia," Autoimmunity Reviews, vol. 16, pp. 620-632, Apr. 17, 2017.
Basheer, A., et al., "Enols of Substituted Cyanomalonamides," J Org. Chem. 72:5297-5312 (2007).
Bastin, R., et al., "Salt Selection and Optimisation Procedures for Pharmaceutical New Chemical Entities," Org. Process Res. Dev, 4:427-435 (2000).
Berge, S., et al., "Pharmaceutical Salts," J Pharm. Sci., 66:1-19 (1977).
Bernhart, C., et al., "Synthesis and Antiarrhythmic activity of New [(Dialkylamino)alkyl]pyridylacetamides," J Med Chem., 26:451-455 (1983).
Bobkova, I., et al., "Modern view on the treatment of membranous nephropathy," Therapeutic archive, vol. 6, pp. 99-104 (2020).
Burchat, A., et al., "Pyrrolo[2,3-d]pyrimidines Containing an Extended 5-Substituent as Potent and Selective Inhibitors of Ick II," Bioorg. Med. Chem. Lett, 10:2171-2174 (2000).
Burini, E., et al., "Efficient Synthesis of 4-Cyano 2,3-Dihydrooxazoles by Direct Amination of 2-Alkylidene 3-Oxo Nitriles," Synlett, 17: 2673-2675 (2005).
Bussel, J., et al., "A randomized, double-blind study of romiplostim to determine its safety and efficacy in children with immune thrombocytopenia," Blood, vol. 118, No. 1, pp. 28-36 (2011).
Caira, M., et al., "Crystalline Polymorphism of Organic Compounds," Topics in Current Chemistry, vol. 198, pp. 163-208 (1998).

(56) References Cited

OTHER PUBLICATIONS

Calderwood, D., et al., "Pyrrolo[2,3-d]pyrimidines Containing Diverse N-7 Substituents as Potent Inhibitors of Lck," Bioorg. Med. Chem. Lett., 12:1683-1686 (2002).
Carruthers, M., et al., "Development of an IgG4-RD Responder Index," International Journal of Rheumatology, vol. 2012, pp. 1-8 (2012).
CAS RN 26272-41-3, STN entered Nov. 16, 1984 (1 page).
Certified English Translation of CN 105753863 A published in Chinese on Jul. 13, 2016 (57 pages).
ClinicalTrial.gov ID No. NCT02704429, "A Study of PRN1008 in Adult Patients With Pemphigus Vulgaris", last update posted Feb. 13, 2023 (49 pages).
ClinicalTrial.gov ID No. NCT03395210, "A Study of Rilzabrutinib in Adult Patients With Immune Thrombocytopenia (ITP)", last update posted Jul. 28, 2023 (18 pages).
ClinicalTrial.gov ID No. NCT03762265, "A Study of PRN1008 in Patients With Pemphigus", last update posted Aug. 2, 2023 (104 pages).
ClinicalTrial.gov ID No. NCT04520451, "Open Label Two-Arm Study to Evaluate Rilzabrutinib in IgG4-Related Disease Patients", last update posted Sep. 7, 2023 (20 pages).
ClinicalTrial.gov ID No. NCT04562766, "Study to Evaluate Rilzabrutinib in Adults and Adolescents With Persistent or Chronic Immune Thrombocytopenia (ITP) (LUNA 3)", last update posted Aug. 21, 2023 (24 pages).
ClinicalTrial.gov ID No. NCT04748926, "Food Effect and Relative Bioavailability Study of Rilzabrutinib in Healthy Participants", last update posted Apr. 25, 2022 (20 pages).
ClinicalTrial.gov ID No. NCT05002777, "Efficacy, Safety and Pharmacokinetics of Rilzabrutinib in Patients With Warm Autoimmune Hemolytic Anemia (wAIHA)", last update posted Jul. 27, 2023 (20 pages).
ClinicalTrial.gov ID No. NCT05018806, "Proof of Concept Study of Rilzabrutinib in Adult Patients With Moderate-to- severe Atopic Dermatitis", last update posted Jul. 6, 2023 (23 pages).
ClinicalTrial.gov ID No. NCT05104892, "Proof of Concept Study of Rilzabrutinib in Adult Participants With Moderate-to-severe Asthma", last update posted Aug. 21, 2023 (25 pages).
ClinicalTrial.gov ID No. NCT05107115, "Rilzabrutinib for the Treatment of Chronic Spontaneous Urticaria in Patients Who Remain Symptomatic Despite the Use of H1 Antihistamine (RILECSU)", last update posted Aug. 24, 2023 (22 pages).
Cohen, M., et al., "Structural Bioinformatics-Based Design of Selective, Irreversible Kinase Inhibitors," Science, 308:1318-1321 (2005).
Cuker, A., et al., "How I treat refractory immune thrombocytopenia," Blood, vol. 128, No. 12, pp. 1547-1554, Sep. 22, 2016.
Database Biosis [Online], Biosciences Information Service, Kuter, D., et al., "Cognitive Impairment Among Patients with Chronic Immune Thromocytopenia," Blood, vol. 140, suppl. 1, pp. 8422-8424 (2022).
Database Biosis [Online], Biosciences Information Service, Langrish, C., et al., "PRN1008, a Reversible Covalent BTK Inhibitor in Cinical Development for Immune Thrombocytopenia Purpura," Blood, vol. 130, suppl. 1, p. 1052 (2017).
Database Embase [Online], Elsevier Science Publishers, Kuter, D., "Oral Rilzabrutinib, a Bruton Tyrosine Kinase Inhibitor, Showed Clinically Active and Durable Platelet Responses and Was Well-Tolerated in Patients with Heavily Pretreated Immune Thrombocytopenia," Blood, vol. 136, suppl. 1, pp. 20201205-20201208 (2020).
Database Embase [Online], Elsevier Science Publishers, Kuter, D., "Updated main study period and long-term extension (LTE) results with oral Bruton tyrosine kinase inhibitor rilzabrutinib in immune thrombocytopenia (ITP)," Research and Practice in Thrombosis and Haemostasis, vol. 6, suppl. 1 (2022).
Deng, Y., et al., "Reversible phospho-Smad3 signalling between tumour suppression and fibrocarcinogenesis in chronic hepatitis B infection," Clin. Exp. Immunol., 176:102-111 (2013).
Dias, A., et al., "Ibrutinib: A New Frontier in the Treatment of Chronic Lymphocytic Leukemia by Bruton's Tyrosine Kinase Inhibition," Cardiovasc Hematol Agents Med Chem, 11 (4):265-271 (2013).
Dick, et al., "Pemphigus: A treatment update," Autoimmunity 2009, vol. 39, No. 7, pp. 591-599 (Jul. 7, 2009).
Donald, A., et al., "Rapid Evolution of 6-Phenylpurine Inhibitors of Protein Kinase B through Structure-Based Design," J Med. Chem., 50:2289-2292 (2007).
Elinson, M., et al., "Electrochemical transformation of cyanoacetic ester and alkylidenecyanoacetic esters into 3-substituted 1,2-dicyanocyclopropane-1,2-dicarboxylates," Russian Chemical Bulletin, 47(6):1133-1136 (1998).
Elliott, M., et al., "Insecticidal activity of the Pyrethrins and Related Compounds x. • 5-Benzyl-3-furylmethyl 2,2-dimethylcyclopropanecarboxylates with ethylenic substituents at position 3 on the cyclopropane ring," Pestic. Sci., 7: 499-502 (1976).
Elliott, M., et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry, vol. 21, 2470-2474 (1972-1999) (1974).
English Language Abstract for JP 42008308 B4, published Apr. 8, 1967, by Yoshitomi Pharmaceutical Industries, Ltd. (1 page).
English Translation of Office Action issued Apr. 12, 2013, in Chinese Application No. 201080061570.1.
Hill, Q.A., et al., "The diagnosis and management of primary autoimmune haemolytic anaemia," British Journal of Haematology, vol. 176, No. 3, pp. 395-411 (2017).
Hodgson, K., et al., "Autoimmune cytopenia in chronic lymphocytic leukemia: diagnosis and treatment," British Journal of Haematology, vol. 154, No. 1, pp. 14-22 (2011).
Honigberg, L.A., et al., "The Bruton tyrosine kinase inhibitor PCT-32765 blocks B-cell activation and is efficacious in models of autoimmune disease and B-cell malignancy," PNAS, vol. 107, pp. 13075-13080 (2010).
Horvath, B., et al., "Low dose rituximab is effective in pemphigus," British Journal of Dermatology, vol. 166, No. 2, pp. 405-412 (2012).
Hu, Chongmao, "Production and Application of a Pharmaceutical Excipient—Thin Film Coating," Beijing: China Medical Science Press, p. 14 (May 31, 2014).
Hu, Rongfeng, "Industrial Pharmaceutics," Beijing: China Press of Traditional Chinese Medicine, pp. 237-239 (Jul. 31, 2010).
Hutcheson, J., et al., "Modulating proximal cell signaling by targeting Btk ameliorates humoral autoimmunity and end-organ disease in murine lupus," Arthritis Research & Therapy, vol. 14, pp. R243 (2012).
Ihrke, P.J., et al., "Pemphigus foliaceus in dogs: a review of 37 cases," Journal of the American Veterinary Medical Association, vol. 186, No. 1, pp. 59-66 (1985).
International Search Report for PCT/US2020/065689 mailed on Apr. 29, 2021 (9 pages).
Irwin, S., "Comprehensive observational assessment: Ia. A systematic, quantitative procedure for assessing the behavioral and physiologic state of the mouse," Psychopharmacologia, vol. 13, No. 3, pp. 222-257 (1968).
Ito, M., et al., "Bruton's tyrosine kinase is essential for NLRP3 inflammasome activation and contributes to ischaemic brain injury," Nature Communications, vol. 6, No. 1, p. 1 (2015).
Ivankovic, S., Fehlende teratogene Wirkung von Nitroprussidnatrium (NNP) an Wistar-Ratten und Kaninchen [Absence of a teratogenic effect of sodium nitroprusside in wistar rats and rabbits (author's transl)]. Arzneimittelforschung, vol. 29, No. 8, pp. 1092-1094 (1979).
Jager, U., et al., "Diagnosis and treatment of autoimmune hemolytic anemia in adults: Recommendations from the First International Consensus Meeting," Blood Review, vol. 41, p. 100648 (2020).
Joly, P., et al., "First-line rituximab combined with short-term prednisone versus prednisone alone for the treatment of pemphigus (Ritux 3): a prospective, multicentre, parallel-group, open-label randomised trial," Lancet, vol. 389, No. 10083, pp. 2031-2040 (2017).

(56) References Cited

OTHER PUBLICATIONS

Joly, P., et al., "Pemphigus group (vulgaris, vegetans, foliaceus, herpetiformis, brasiliensis)," Clinical Dermatology, vol. 29, No. 4, pp. 432-436 (2011).

Kamaly, Nazila, et al., "Degradable Controlled-Release Polymers and Polymeric Nanparticles: Mechanisms of Controlling Drug Release," Chemical Reviews, vol. 116, pp. 2602-2663 (Feb. 8, 2016).

Karra, E., et al., "The role of peptide YY in appetite regulation and obesity," Journal of Physiology, vol. 587, No. 1, pp. 19-25 (2009).

Khellaf, M., et al., "Safety and efficacy of rituximab in adult immune thrombocytopenia: results from a prospective registry including 248 patients," Blood, vol. 124, No. 22, pp. 3228-3236 (2014).

Kihlman, B.A., "Experimentally Induced Chromosome Aberrations in Plants, I. The production of chromosome aberrations by cyanide and other heavy metal complexing agents," Journal of Biophysical & Biochemical Cytology, vol. 3, No. 3, pp. 363-380 (1957).

Kim, K.H., et al., "Imidazo[1.5-a]quinoxalines as irreversible BTK inhibitors for the treatment of rheumatoid arthritis," Bioorganic & Medicinal Chemical Letters, vol. 21, pp. 6258-6263 (2011).

Klein, N.P., et al., "Rates of autoimmune diseases in Kaiser Permanente for use in vaccine adverse event safety studies," Vaccine, vol. 28, No. 4, pp. 1062-1068 (2010).

Kohrt, H.E., et al., "Ibrutinib antagonizes rituximab-dependent NK cell-mediated cytotoxicity," Blood, vol. 123, No. 12, pp. 1957-1960 (2014).

Kridin, K., et al., "Mortality and Cause of Death in Patients with Pemphigus," Acta Dermato-Venereologica, vol. 97, No. 5, pp. 607-611 (2017).

Kuter, D.J., et al., "22 oral rilzabrutinib Bruton tyrosine kinase inhibitor, showed clinically active and durable platelet responses and was well-tolerated in patients with heavily pretreated immune thrombocytopenia," 62nd ASH Annual Meeting & Exposition, Abstract (presentation) (Dec. 5-8, 2020).

Kuter, D.J., et al., "Phase I/II, open-label, adaptive study of oral tyrosine inhibitor patients with relapsed/refractory primary or secondary immune thrombodytopenia," Blood, vol. 134 (Suppl 1), p. 87 (2019).

Kuter, D.J., et al., "Rilzabrutinib, an Oral BTK Inhibitor, in Immune Thrombocytopenia," MEJM Paper, vol. 386, No. 15, pp. 1421-1431 (2022).

Kuter, D.J., et al., "Safety and efficacy of rilzabrutinib (PRN1008), an oral Bruton tyrosine kinase inhibitor, in relapsed/refractory patients with primary or secondary immune thrombocytopenia: Phase I/II adaptive study," European Hematology Association (EHA) annual meeting, vol. 4, No. S1, pp. 118-119 (abstract S316) poster presentation (2020).

Langrish, C., et al., Preclinical Efficacy and Anti-Inflammatory Mechanisms of Action of the Bruton Tyrosine Kinase Inhibitor Rilzabrutinib for Immune-Mediated Disease, Journal of Immunology, vol. 206, No. 7, pp. 1454-1486 (2021).

Lindberg, H.A., et al., "Observations of the Pathologic Effects of Thiocyanate: An Experimental Study," American Heart Journal, vol. 21, No. 5, pp. 605-616 (1941).

Lipsky, A., et al., Managing toxicities of Bruton tyrosine kinase inhibitors, Hematology, American Society of Hematology Education Program, vol. 2020, No. 1, pp. 336-345 (2020).

Mahoney, M.G., et al., "Explanations for the clinical and microscopic localization of lesions in pemphigus foliaceus and vulgaris," Journal of Clinical Investigation, vol. 103, No. 4, pp. 461-468 (1999).

Maronpot, R.R., et al., "Hepatic Enzyme Induction: Histopathology," Toxicologic Pathology, vol. 38, pp. 776-795 (2010).

Martin, Y.C., et al., "Do structurally similar molecules have similar biological activity?," Journal of Medicinal Chemistry, vol. 45, No. 19, pp. 4350-4538 (2002).

Masters, S.L., et al., "Activation of the NLRP3 inflammasome by islet amyloid polypeptide provides a mechanism for enhanced IL-1Beta in type 2 diabetes," Nature Immunology, vol. 11, No. 10, pp. 897-904 (2010).

McKenzie, C.G., et al., "Cellular immune dysfunction in immune thrombocytopenia," British Journal of Haematology, vol. 163, pp. 10-23 (2013).

Metz, M., et al., "Fenebrutinib in H1 antihistamine-refractory chronic spontaneous urticaria: a randomized phase 2 trial," Nature Medicine, vol. 27, No. 11, pp. 1961-1969 (2021).

Michel, M., "Classification and therepeutic approaches in autoimmune hemolytic anemia: an update," Expert Review of Hematology, vol. 4, No. 6, pp. 607-618 (2011).

Michel, M., et al., "A randomized and double-blind controlled trial evaluating the safety and efficacy of rituximab for warm autoimmune hemolytic anemia in adults (the RAIHA study)," American Journal of Hematology, vol. 92, No. 1, pp. 23-27 (2017).

Mohamed, A.J., et al., Bruton's tyrosine kinase (Btk): function, regulation, and transformation with special emphasis on the PH domain, Immunology Review, vol. 228, pp. 58-73 (2009).

Montillo, M., et al., "Ibrutinib in previously treated chronic lymphocytic leukemia patients with autoimmune cytopenias in the Resonate study," Blood Cancer Journal 7, No. e524 Letter to the Editor (2017).

Mosher, K.I., et al., "Go with your gut: microbiota meet microglia," Nature Neuroscience, vol. 18, pp. 930-931 (2015).

Murrell, D.F., et al., "Diagnosis and Management of Pemphigus: recommendations by an International Panel of Experts," Journal of American Academy of Dermatology (2018).

Nagasawa, H., et al., "Inhibitory effects of potassium thiocyanate on normal and neoplastic mammary development in female mice," European Journal of Cancer, vol. 16, No. 4, pp. 473-480 (1980).

Newman, K., et al., "Management of immune cytopenias in patients with systemic lupus erythematosus," Autoimmunity Reviews, vol. 12, No. 7, pp. 784-791 (2013).

Neys, S., et al., "Targeting Bruton's Tyrosine Kinase in Inflammatory and Autoimmune Pathologies," Frontiers in Cell & Developmental Biology, vol. 9, p. 668131 (2021).

Palmer, R.S., et al., "Clinical use of Potassium Sulfocyanate in Hypertension: A Preliminary Report of 59 Cases," New England Journal of Medicine, vol. 201, No. 15, pp. 709-714 (1929).

Peng, Tingting, et al., "Data on the drug release profiles and powder characteristics of the ethyl cellulose based microparticles prepared by the ultra-fine particle processing system," Data in Brief, vol. 29, pages, No. 105629, pp. 1-6 (Feb. 8, 2020).

Porro, A.M., et al., "Pemphigus vulgaris," Anais Brasileiros de Dermatologia, vol. 94, No. 3, pp. 264-278 (2019).

Press Release, "Sanofi to acquire Principia Biopharma," Aug. 17, 2020.

Rankin, A.L., et al., "Selective inhibition of BTK prevents murine lupus and antibody-mediated glomerulonephritis," Journal of Immunology, vol. 191, No. 9, pp. 4540-4550 (2012).

Kamath, S., et al., "Receptor-Guided Alignment-Based Comparative 3D-QSAR Studies of Benzylidene Malonitrile Tyrphostins as EGFR and HER-2 Kinase Inhibitors," J Med. Chem., 46:4657-4668 (2003).

Kamijo, S., et al., "Tetrazole synthesis via the palladium-catalyzed three component coupling reaction," MolecularDiversity, 6: 181-192 (2003).

Kamisawa, T., et al., "IgG4-related disease", The Lancet, vol. 385, No. 9976, pp. 1460-1471 (2015).

Kanwar, A., et al., "Rituximab in Pemphigus," Indian J Dermatol. Venereal. Leprol. [serial online], 78:671-676 (2012).

Kholodov, et al., "Clinical Pharmacokinetics," Medicine, pp. 83-98, 134-138, 160, 378-380 (1985).

Khosroshani, A., et al., "Rituximab for the treatment of IgG4-Related Disease," Medicine, vol. 91, pp. 57-66 (2012).

Knight, Z., et al., "A membrane capture assay for lipid kinase activity," Nat Protoc., 2(10):2459-2466 (2017).

Kojima, S., et al. "Stereoselective synthesis of activated cyclopropanes with an alpha-pyridinium acetamide bearing an 8-phenylmethyl group as the chiral auxiliary," Tetrahedron Lett., 45(18): 3565-3568 (2004).

(56) References Cited

OTHER PUBLICATIONS

Komura, K., et al., "Layered silicate PLS-1: A new solid base catalyst for C-C bond forming reactions," Catal Commun., 8(4): 644-648 (2007).
Kotz, A., et al., "The Action of Chloroform on Methylene and Metheny! Groups," Journal fuer Praktische Chemie (Leipzig), Abstract, 74: 425-48 (1907).
Kuter, D., et al., "LUNA3 Phase III Multicenter, Double-Blind, Randomized, Placebo-Controlled Trial of the Oral BTK Inhibitor Rilzabrutinib in Adults and Adolescents with Persistent or Chronic Immune Thrombocytopenia," Blood, vol. 138, supplement 1, p. 1010 (2021).
Kuter, D., et al., "Rilzabrutinib versus placebo in adults and adolescents with persistent or chronic immune thrombocytopenia: LUNA3 phase III study," Therapeutic Advances in Hematology, vol. 14, pp. 1-14 (2023).
Langrish, C., et al., "PRN1008, a Reversible Covalent BTK Inhibitor in Clinical Development for Immune Thrombocytopenia Purpura," Blood, vol. 130, suppl. 1, No. 1052 (2017).
Leopold, C., "A Practical Approach in the Design of Colon-specific Drug Delivery System," Wiley-VCH; Drug Targeting Organ-Specific Strategies, Chapter 6, pp. 157-170 (2001).
Liang, C., et al., "The development of Bruton's tyrosine kinase (BTK) inhibitors from 2012 to 2017: A mini-review," European Journal of Medicinal Chemistry, vol. 151, pp. 315-326 (2018).
Liu, J., et al., "Emerging small-molecule inhibitors of the Bruton's tyrosine kinase (BTK): Current development", European Journal of Medicinal Chemistry, vol. 217, Mar. 12, 2021, p. 113329.
Lou, Y., et al., "Bruton's Tyrosine Kinase Inhibitors: Approaches to Potent and Selective Inhibition, Preclinical and Clinical Evaluation for Inflammatory Diseases and B Cell Malignancies," J Med. Chem., 55(10): 4539-4550 (2012).
Maas, S., et al., "Conjugate Addition of Dialkylaluminum Chlorides to Alkylidenemalonic Acid Derivatives," Synthesis, vol. 10, pp. 1792-1798 (1999).
Mahajan, V., et al., "IgG4-Related Disease," Annual Review of Pathology: Mechanisms of Disease, vol. 9, pp. 315-347 (2014).
Maurya, R., et al., "Catalyst-free stereoselective cyclopropanation of electron deficient alkenes with ethyl diazoacetate," RSC Advances, vol. 3, pp. 15600-15603 (2013).
MedicineNet.com. Definition of Cancer. Web: (2004).
MedlinePlus. Autoimmune Diseases, Web: (2014).
Meydan, N., et al., "Inhibition of acute lymphoblastic leukaemia by a Jak-2 inhibitor," Nature, vol. 379, pp. 645-648 (1996).
Miller, R., "Electrophilic Fragment-Based Design of Reversible Covalent Kinase Inhibitors," Journal of the American Chemical Society, vol. 135, No. 14, pp. 5298-5301 (2013).
Murrell, D., et al., "A Pilot Study of the Efficacy of a Bruton's Tyrosine Kinase Inhibitor in the Treatment of Dogs with Pemphigus Foliaceus", Australasian Journal of Dermatology, vol. 58, No. S1, p. 73 (Jan. 1, 2017).
Nakamura, M. et al., "Diquafosol Ophthalmic Solution for Dry Eye Treatment," Advances in Therapy, vol. 29, No. 7, pp. 579-589 (2012).
Outerbridge, C., et al., "A new treatment for autoimmune blistering diseases—the efficacy of the Bruton's tyrosine kinase inhibitor PRN473 in canine pemphigus foliaceus," Journal of American Academy of Dermatology, No. 3530, p. AB141 (2016).
Pan, Z. et al., "Discovery of Selective Irreversible Inhibitors for Bruton's Tyrosine Kinase," ChemMedChem, vol. 2, pp. 58-61 (2007).
Patani, G., et al., "Bioisosterism: A Rational Approach in Drug Design," Chemical Reviews, vol. 96, pp. 3147-3176 (1996).
Pennington, L., et al., "The Necessary Nitrogen Atom: A Versatile High-Impact Design Element for Multiparameter Optimization," Journal of Medicinal Chemistry, vol. 60, No. 9, pp. 3552-3579 (2017).
Porter, D., et al., "The discovery of potent, orally bioavailable pyrimidine-5-carbonitrile-6-alkyl CXCR2 receptor antagonists," Bioorganic and Medicinal Chemistry Letters, vol. 24, pp. 3285-3290 (2014).
Principia Biopharma: "A Study of PRN1008 in Adult Patients with Pemphigus Vulgaris", ClinicalTrials.gov, (Mar. 10, 2016).
Proenca, F., et al., "A simple and eco-friendly approach for the synthesis of 2-imino and 2-oxo-2H-chromene-3-carboxamides, "Green Chemistry, vol. 10, pp. 995-998 (2008).
Rellos, P., et al., "Structure and Regulation of the Human Nek2 Centrosomal Kinase," Journal of Biological Chemistry, vol. 282, No. 9, pp. 6833-6842 (2007).
Robak, T., et al., "Tyrosine kinase inhibitors as potential drugs for B-cell lymphoid malignancies and autoimmune disorders," Expert Opinion on Investigational Drugs, vol. 21, No. 7, pp. 921-947 (2012).
Rodeghiero, F., "A critical appraisal of the evidence for the role of splenectomy in adults and children with ITP," British Journal of Haematology, vol. 181, No. 2, pp. 183-195 (2018).
Sammes, M., et al., "α-Cyano-sulphonyl Chlorides: Their Preparation and Reactions with Amines, Alcohols, and Enamines," Journal of the Chemical Society, pp. 2151-2155 (1971).
Sanofi Press Release: Rilzabrutinib LUNA 3 phase 3 study met primary endpoint in immune thrombocytopenia, Apr. 23, 2024.
Santilli, A., et al., "8,9,10,11-Tetrahydro-12H-benzo[5,6]quinoxalino[2,3-e][1,4]diazepin-12-ones. Examples of a New Heterocyclic Ring System," Journal of Organic Chemistry, vol. 29, pp. 2066-2068 (1964).
Santus, G., et al., "Osmotic Drug Delivery: A Review of the Patent Literature," Journal of Controlled Release, vol. 35, pp. 1-21 (1995).
Schwarz, J., et al., "Novel Cyclopropyl β-Amino Acid Analogues of Pregabalin and Gabapentin That Target the α2-δ Protein," Journal of Medicinal Chemistry, vol. 48, pp. 3026-3035 (2005).
Schwobel, J., et al., "Prediction of Michael-Type Acceptor Reactivity toward Glutathione," Chemical Research in Toxicology, vol. 23, pp. 1576-1585 (2010).
Smith, P., et al., "A phase I trial of PRN1008, a novel reversible covalent inhibitor of Bruton's tyrosine kinase, in healthy volunteers: A phase I study of PRN1008", British Journal of Clinical Pharmacology, vol. 83, No. 11, pp. 2367-2376 (Aug. 1, 2017).
Stahl, P., et al., (Eds.) Handbook of Pharmaceutical Salts: Properties, Selection, and Use, Wiley-VCH; pp. 1-374 (2002).
Stevens, C., et al., "Synthesis of Substituted Cyclopropylphosphonates by Michael Induced Ring Closure (MIRC) Reactions," Synlett, vol. 7, pp. 1089-1092 (2002).
Stone, J., et al., "Recommendations for the nomenclature of IgG4-related disease and its individual organ system manifestations," Arthritis Rheumatology, vol. 64, No. 10, pp. 3061-3067 (2012).
Structure-Based Search Results (May 10, 2011, 10:04 AM), SciFinder.
Structure-Based Search Results (May 10, 2011, 10:20 AM), SciFinder.
Structure-Based Search Results (May 10, 2011, 10:46 AM), SciFinder.
Structure-Based Search Results (May 9, 2011, 8:13 PM), SciFinder.
Rip, J., et al., "The role of Bruton's tyrosine kinase in immune cell signaling and systemic autoimmunity," Critical Reviews in Immunology, vol. 38, No. 1, pp. 17-62 (2018).
Rogers, K.A., et al., "Incidence and description of autoimmune cytopenias during treatment with ibrutinib for chronic lymphocytic leukemia," Leukemia, vol. 30, pp. 346-350 (2016).
Roumier, M., et al., "Characteristics and outcome of warm autoimmune hemolytic anemia in adults: New insights based on a single-center experience with 60 patients," American Journal of Hematology, vol. 89, No. 9, pages E150-E155 (2014).
Sadeghi, Fatemeh, et al., "The influence of drug type of the release profiles from Surelease-coated pellets," International Journal of Pharmaceuticals, vol. 254, pp. 123-135 (2003).
Saloojee, Y., et al., "Carboxyhaemoglobin and plasma thiocyanate: complementary indicators of smoking behaviour," Thorax, vol. 37, No. 7, pp. 521-525 (1982).
Schwab, I., et al., "Intravenous immunoglobulin therapy: how does IgG modulate the immune system?," Nature Reviews Immunology, vol. 13, pp. 176-189 (2013).

(56) References Cited

OTHER PUBLICATIONS

Serafimova, I.M., et al., "Reversible targeting of noncatalytic cysteines with chemically tuned electrophiles," Nature Chemical Biology, vol. 8, No. 5, pp. 471-476 (2012).
Shekunov, B Y et al., "Crystallization processes in pharmaceutical technology and drug delivery design", Journal of Crystal Growth, vol. 211, No. 104, Apr. 1, 2000, pp. 122-136.
Sideras, P., et al., "Molecular and cellular aspects of X-linked agammaglobulinemia," Advanced Immunology, vol. 59, pp. 135-223 (1995).
Storim, J., et al., "Dose-finding Phase 2 study to evaluate the efficacy and safety of the novel BTK inhibitor LOU064 in patients with CSU inadequately controlled by H1-antihistamines," Poster from 28th European Academy of Dermatology and Venereology Congress, Oct. 9-13, 2019 in Madrid, Spain.
Streicher, E., et al., "Distribution of thiocyanate between plasma and cerebrospinal fluid," American Journal of Physiology, vol. 206, No. 2, pp. 251-254 (1964).
Tan, S., et al., "Targeting the SYK-BTK axis for the treatment of immunological and hematological disorders: Recent progress and therapeutic perspectives," Pharmacological Therapy, vol. 138, No. 2, pp. 294-309 (2013).
Taylor, I., et al., "Comparison of longevity and common tumor profiles between Sprague-Dawley and Han Wistar rats," Journal of Toxicology & Pathology, vol. 33, pp. 189-196 (2020).
Unniappan, S., et al., "Leptin extends the anorectic effects of chronic PYY (3-36) administration in ad libitum-fed rats," American Journal of Physiology-Regulatory, Integrative and Comparitive Physiology, vol. 295, No. 1, pp. R51-R58 (2008).
Weber, A.N., "Targeting the NLRP3 Inflammasome via BTK," Frontiers in Cell and Developmental Biology, vol. 9, p. 630479 (2021).
Weber, A.N., et al., "Bruton's tyrosine kinase: an emerging key player in innate immunity," Frontiers in Immunology, vol. 8, p. 1454 (2017).
Weber, K., "Differences in types and incidence of neoplasms in Wistar Han and Sprague-Dawley rats," Toxicology & Pathology, vol. 45, No. 1, pp. 64-75 (2017).
Wree, A., et al., "NLRP3 inflammasome activation results in hepatocyte pyroptosis, liver inflammation, and fibrosis in mice," Hepatology, vol. 59, No. 3, pp. 898-910 (2014).
Xu, D., et al., "RN486, a selective Bruton's tyrosine kinase inhibitor, abrogates immune hypersensitivity responses and arthritis in rodents," Journal of Pharmacology & Experimental Therapy, vol. 341, pp. 90-103 (2012).
Yamaguchi, T., "Mutagenicity of Isothiocyanates, Isocyanates and Thioureas on *Salmonella typhimurium*," Agricultural Biology & Chemistry, vol. 44, No. 12, pp. 3017-3018 (1980).
Zanella, A., et al., "Treatment of autoimmune hemolytic anemias," Haematologica, vol. 99, No. 10, pp. 1547-1554 (2014).
Zhang, D., et al., "Recent Advances in BTK Inhibitors for the Treatment of Inflammatory and Autoimmune Diseases," Molecules, vol. 26, No. 16, p. 4907 (2021).
Advani, R.H., et al., "Bruton tyrosine kinase inhibitor ibrutinib (PCI-32765) has significant activity in patients with relapsed/refractory B-cell malignancies," Journal of Clinical Oncology, vol. 31, No. 1, pp. 88-94 (2013).
American College of Rheumatology; ACR COVID-19 Vaccine Clinical Guidance Task Force, "COVID-19 vaccine clinical guidance summary for patients with rheumatic and musculoskeletal diseases," https://www.rheumatology.org/Portals/0/Files/COVID-19-Vaccine-Clinical-Guidance-Rheumatic-Diseases-Summary.pdf, cited May 10, 2021.
Anderson, R.C., et al., "Absorption and Toxicity of Sodium and Potassium Thiocyanates," Journal of American Pharmacists Association, vol. 29, No. 4, pp. 152-161 (1940).
Banerjee, K.K., et al., "Effect of thiocyanate ingestion through milk on thyroid hormone homeostasis in women," British Journal of Nutrition, vol. 78, No. 5, pp. 679-681 (1997).
Barcellini, W., et al., "Clinical heterogeneity and predictors of outcome in primary autoimmune hemolytic anemia: a GIMEMA study of 308 patients," Blood, vol. 124, No. 19, pp. 2930-2936 (2014).
Barker, M.H., "The Blood Cyanates in the Treatment of Hypertension," Journal of American Medical Association, vol. 106, No. 10, pp. 762-767 (1936).
Barker, M.H., et al., "Further Experiences with Thiocyanates," Journal of American Medical Association, vol. 117, No. 9, pp. 1591-1594 (1941).
Bartsch, R., et al., "Human relevance of follicular thyroid tumors in rodents caused by non-genotoxic substances," Regulatory Toxicology & Pharmacology, vol. 98, pp. 199-208 (2018).
Beissert, S., et al., "A comparison of oral methylprednisolone plus azathioprine or mycophenolate mofetil for the treatment of pemphigus," Archives of Dermatology, vol. 142, No. 11, pp. 1447-1454 (2006).
Bhandari, R.K., et al., "Cyanide toxicokinetics: the behavior of cyanide, thiocyanate and 2-amino-2-thiazoline-4-carboxylic acid in multiple animal models," Journal of Analytical Toxicology, vol. 38, No. 4, pp. 218-225 (2014).
Bizikova, P., et al., "Cloning and establishment of canine desmocollin-1 as a major autoantigen in canine pemphisgus foliaceus," Veterinary Immunology & Immunopathology, vol. 149, pp. 197-207 (2012).
Bizikova, P., et al., "Serum autoantibody profiles of IgA, IgE and IgM in canine pemphigus foliaceus," Veterinary Dermatology, vol. 25, pp. 471-475 (2014).
Bolon, B., et al., "STP Position Paper: Recommended Practices for Sampling and Processing the Nervous System (Brain, Spinal Cord, Nerve, and Eye) during Nonclinical General Toxicity Studies," Toxicologic Pathology, vol. 41, pp. 1028-1048 (2013).
Borthakur, G., et al., "Immune anaemias in patients with chronic lymphocytic leukaemia treated with fludarabine, cyclophosphamide and rituximab—incidence and predictors," British Journal of Haematology, vol. 136, No. 6, pp. 800-805 (2007).
Boulos, B.M., et al., "Placental transfer of antipyrine and thiocyanate and their use in determining maternal and fetal body fluids in a maintained pregnancy," Archives Internacionales de Pharmacodynamie et de Therapie, vol. 201, No. 1, pp. 42-51 (1973).
Bradshaw, J.M., et al., "Prolonged and tunable residence time using reversible covalent kinase inhibitors," Nature Chemical Biology, vol. 11, No. 7, pp. 525-531 (2015).
Brodsky, R.A., "Warm Autoimmune Hemolytic Anemia," New England Journal of Medicine, vol. 381, No. 7, pp. 647-654 (2019).
Brown, J.R., et al., "Phase I study of single-agent CC-292, a highly selective Bruton's tyrosine kinase inhibitor, in relapsed/refractory chronic lymphocytic leukemia," Haematologica, vol. 101, p. e295 (2016).
Burger, J.A., "Bruton Tyrosine Kinase Inhibitors: Present and Future," Cancer Journal, vol. 25, No. 6, pp. 386-393 (2019).
Burger, J.A., et al., "Randomized Trial of Ibrutinib Versus Ibrutinib Plus Rituximab (Ib+R) in Patients with Chronic Lymphocytic Leukemia (CLL)," Blood, vol. 130, p. 427 (2017).
Bussel, J.B., et al., "Eltrombopag for the treatment of chronic idiopathic thrombocytopenia purpura," New England Journal of Medicine, vol. 357, pp. 2237-2247 (2007).
Butt, M.T., et al., "Nervous System: Astrocytosis," In Toxicologic Pathology Nonclinical Safety Assessment, Sahota, P.S., Popp, J.A., Hardistry, J.F., and Gopinath, C. (eds), vol. 20, pp. 901-903 (2013).
Byrd, J.C., et al., "Acalabrutinib (ACP-196) in relapsed chronic lymphocytic leukemia," New England Journal of Medicine, vol. 374, No. 4, pp. 323-332 (2016).
Carnero-Contentti, E., et al., "Bruton's tyrosine kinase inhibitors: a promising emerging treatment option for multiple sclerosis," Expert Opinion on Emerging Drugs, vol. 25, No. 4, pp. 377-381 (2020).
Chandler, J.D., et al., "Biochemical Mechanisms and Therapeutic Potential of the Pseudohalide Thiocyanate in Human Health," Free Radical Research, vol. 49, No. 6, pp. 695-710 (2015).
Chang, B.Y., et al., "The Bruton tyrosine kinase inhibitor PCI-32765 ameliorites autoimmune arthritis by inhibition of multiple effector cells," Arthritis Research & Therapy, vol. 13, No. 4, p. R115 (2011).

(56) References Cited

OTHER PUBLICATIONS

Chaplin, H., Jr., "Clinical usefulness of specific antiglobulin reagents in autoimmune hemolytic anemias," Hematology Program, vol. 8, pp. 25-49 (1973).
Chaudhri, O.B., et al., "Can Gut Hormones Control Appetite and Prevent Obesity?," Diabetes Care, vol. 31, pp. S284-S289 (2008).
Chen, J.F., et al., "The clinical significance of circulating B cells and secreting anti-glycoprotein IIb/IIIa antibody and platelet glycoprotein IIb/IIIa in patients with primary immune thrombocytopenia," Hematology, vol. 15, pp. 283-290 (2013).
Chinese Pharmacopoeia Commission, "The Third Supplement of the Pharmacopoeia of People's Republic of China (Edition 2010)," Beijing: China Medical Science Press, p. 213 (Nov. 30, 2014).
Code of Federal Regulations, Title 21, Chapter II, Part 1308, Schedules of Controlled Substances, Mar. 12, 2021.
Crowther, M., et al., "Evidence-based focused review of the treatment of idiopathic warm immune hemolytic anemia in adults," Blood, vol. 118, No. 15, pp. 4036-4040 (2011).
Cui, Cheng, et al., "Factors Contributing to Drug Release From Enteric-Coated Omeprazole Capsules: An In Vitro and In Vivo Pharmacokinetic Study and IVIVC Evaluation in Beagle Dogs," Nanotechnology and Microtechnology in Drug Delivery Systems, vol. Jan.-Mar. 2020, pp. 1-13 (Jan. 7, 2020).
DeSilva, A., et al., "Gut Hormones and Appetite Control: A Focus on PYY and GLP-1 as Therapeutic Targets in Obesity," Gut Liver, vol. 6, No. 1, pp. 10-20 (2012).
Dierickx, D., et al., "Rituximab in autoimmune haemolytic anaemia and immune thrombocytopenia purpura: a Belgian retrospective multicentric study," Journal of Internal Medicine, vol. 266, No. 5, pp. 484-491 (2009).
DiPaolo, J.A., et al., "Specific Btk inhibition suppresses B cell- and myeloid cell-mediated arthritis," Nature Chemical Biology, vol. 7, pp. 41-50 (2011).
Dispenza, M.C., et al., "Bruton's tyrosine kinase inhibition effectively protects against human IgE-mediated anaphylaxis," Journal of Clinical Investigation, vol. 130, No. 9, pp. 4759-4770 (2020).
Eaton, W.W., et al., "Epidemiology of autoimmune diseases in Denmark," Journal of Autoimmunity, vol. 29, No. 1, pp. 1-9 (2007).
Elizondo-Vega, R., et al., "The role of tanycytes in hypothalamic glucosensing," Journal of Cellular and Molecular Medicine, vol. 19, pp. 1471-1482 (2015).
Fayyaz, A., et al., "Haematological manifestations of lupus," Lupus Science & Medicine, vol. 2, No. 1, p. e000078 (2015).
Futatani, T., et al., "Bruton's tyrosine kinase is present in normal platelets and its absence identifies patients with X-linked agammaglobulinaemia and carrier females," British Journal of Haematology, vol. 114, No. 1, pp. 141-149 (2001).
Gao, Y., et al., "Hormones and diet, but not body weight, control hypothalamic microglial activity," Glia, vol. 62, pp. 17-25 (2014).
Garvin, C.F., "The Fatal Toxic Manifestations of the Thiocyanates," Journal of American Medical Association, vol. 112, No. 12, pp. 1125-1127 (1939).
Ghoroi, C., et al., "Multi-faceted characterization of pharmaceutical powders to discern the influence of surface modification", Powder Technology, vol. 236, May 22, 2012, pp. 63-74.
Goodman, T., et al., "Hypothalamic tanycytes—masters and servants of metabolic, neuroendocrine, and neurogenic functions," Frontiers in Neuroscience, vol. 9, p. 387 (2015).
Gordon, R., et al., "Inflammasome inhibition prevents alpha-synuclein pathology and dopaminergic neurodegeneration in mice," Science Translational Medicine, vol. 10, No. 465, p. eaah4066 (2018).
GRAS notification for sodium thiocyanate for use in the lactoperoxidase system, https://www.fda.gov/files/food/published/GRAS-Notice-GRN-753.pdf, Dec. 18, 2017.
Gregoriou, S., et al., "Management of pemphigus vulgaris: challenges and solutions," Clinical, Cosmetic & Investigational Dermatology, vol. 8, pp. 521-527 (2015).

Heneka, M.T., et al., "NLRP3 is activated in Alzheimer's disease and contributes to pathology in APP/PS1 mice," Nature, vol. 492, No. 7434, pp. 674-678 (2013).
Hertl, M., et al., "Pemphigus. S2 Guideline for diagnosis and treatment—guided by the European Dermatology Forum (EDF) in cooperation with the European Academy of Dermatology and Venereology (EADV)," Journal of the European Academy of Dermatology and Venereology, vol. 29, No. 3, pp. 405-414 (2015).
EU Clinical Trials Register, ACT17125, Spain, first entered into EudraCT Dec. 20, 2022 (5 pages).
EU Clinical Trials Register, ACT17207, Germany, first entered into EudraCT Aug. 6, 2021 (5 pages).
EU Clinical Trials Register, ACT17208, Spain, first entered into EudraCT Aug. 5, 2021 (7 pages).
EU Clinical Trials Register, ACT17209, Spain, first entered into EudraCT Jun. 23, 2021 (6 pages).
EU Clinical Trials Register, DFI17124, Czech, first entered into EudraCT Dec. 12, 2017 (8 pages).
EU Clinical Trials Register, DRI17224, Spain, first entered into EudraCT Jul. 15, 2021 (6 pages).
EU Clinical Trials Register, EFC17092, Summary Results, Jul. 29, 2022 (9 pages).
EU Clinical Trials Register, EFC17093, Germany, first entered into EudraCT Oct. 1, 2020 (6 pages).
EU Clinical Trials Register, PRN1008-012, France, first entered into EudraCT Oct. 22, 2018 (6 pages).
Evans, E., et al., "Inhibition of Btk with CC-292 Provides Early Pharmacodynamic Assessment of Activity in Mice and Humans,"J. Pharm. Exp. Ther., 346(2):219-28 (2013).
Fioravanti, S., et al., "Parallel Solution-Phase Synthesis of Acrylonitrile Scaffolds Carrying L-a-Amino Acidic or D-Glycosyl Residues," J Comb. Chem., 8: 808-811 (2006).
Ghoreschi, K., et al., "Janus kinases in immune cell signaling," Immunol Rev., 228:273-287 (2009).
Goldmann, L., et al., "Oral Bruton tyrosine kinase inhibitors block activation of the platelet Fc receptor CD32a (FcgRIIA): a new option in HIT?," Blood Advances, vol. 3, No. 23, pp. 4021-4033 (2020).
Grando, S. "Pemphigus autoimmunity: Hypotheses and realities," Autoimmunity, 45(1):7-35 (2012).
Gyoung, Y., et al., "Regiospecific synthesis of 2-allylated-5-substituted tetrazoles via palladium-catalyzed reaction of nitriles, trimethylsilyl azide, and allyl acetates," Tetrahedron Lett., 41 (21): 4193-4196 (2000).
Hackam, D., et al., "Translation of Research Evidence from Animals to Humans," JAMA, 296(14):1731-1732 (2006).
Hantschel, O., et al., "The Btk tyrosine kinase is a major target of the Bcr-Abl inhibitor dasatinib." PNAS, 104(33): 13283-13288 (2007).
International Preliminary Report on Patentability for International Application No. PCT/US2010/056890, mailed May 22, 2012, by P. Becamel (10 pages).
International Preliminary Report on Patentability for International Application No. PCT/US2021/012211, mailed on Jul. 21, 2022, by X. Wang (11 pages).
International Preliminary Report on Patentability for International Application No. PCT/US2021/014371, mailed Aug. 4, 2022, by S. Baharlou (7 pages).
International Preliminary Report on Patentability for International Application No. PCT/US2022/024806, mailed Oct. 26, 2023, by X. Tang (8 pages).
International Search Report and Written Opinion for International Application No. PCT/US2010/056890, mailed Jul. 28, 2011, by S. Lee (16 pages).
International Search Report and Written Opinion for International Application No. PCT/US2012/038092, mailed Jul. 5, 2012, by A. Schmid (8 pages).
International Search Report and Written Opinion for International Application No. PCT/US2012/038120, mailed Aug. 20, 2012, by I. Helps (10 pages).
International Search Report and Written Opinion for International Application No. PCT/US2012/038135, mailed Jul. 25, 2012, by I. Helps (9 pages).

(56) References Cited

OTHER PUBLICATIONS

International Search Report and Written Opinion for International Application No. PCT/US2012/038163, mailed Jul. 9, 2012, by A. Schmid (8 pages).
International Search Report and Written Opinion for International Application No. PCT/US2012/038214, mailed Feb. 1, 2013, by Y. Kim (12 pages).
International Search Report and Written Opinion for International Application No. PCT/US2013/045266, mailed Sep. 3, 2013, by W. Hoepfner (11 pages).
International Search Report and Written Opinion for International Application No. PCT/US2013/047958, mailed Oct. 1, 2013, by S. Gomez Gallardo (14 pages).
International Search Report and Written Opinion for International Application No. PCT/US2013/053042, mailed Nov. 18, 2013, by M. Kollmannsberger (12 pages).
International Search Report and Written Opinion for International Application No. PCT/US2013/058614, mailed Nov. 5, 2013, by C. Ladenburger (11 pages).
International Search Report and Written Opinion for International Application No. PCT/US2015/000303, mailed Mar. 21, 2016, by J. Konter (12 pages).
International Search Report and Written Opinion for International Application No. PCT/US2015/000515, mailed Apr. 18, 2016, by M. Kollmannsberger (11 pages).
International Search Report and Written Opinion for International Application No. PCT/US2015/016963, mailed Apr. 22, 2015, by T. Albayrak (10 pages).
International Search Report and Written Opinion for International Application No. PCT/US2015/066868, mailed Mar. 9, 2016, by S. Allnutt (13 pages).
International Search Report and Written Opinion for International Application No. PCT/US2016/035588, mailed Aug. 16, 2016, by W. Hoepfner (10 pages).
International Search Report and Written Opinion for International Application No. PCT/US2016/039070, mailed Oct. 6, 2016, by R. Saez Diaz (18 pages).
International Search Report and Written Opinion for International Application No. PCT/US2017/040075, mailed Oct. 2, 2017, by M. Ceyte (9 pages).
International Search Report and Written Opinion for International Application No. PCT/US2020/054809 mailed Jan. 25, 2021, by S. Collins (12 pages).
International Search Report and Written Opinion for International Application No. PCT/US2020/055410 mailed on Jan. 15, 2021, by A. Jakobs (8 pages).
International Search Report and Written Opinion for International Application No. PCT/US2020/065689, mailed on Apr. 29, 2021, by J. Guspanova (17 pages).
International Search Report and Written Opinion for International Application No. PCT/US2021/012211 mailed on Apr. 9, 2021, by B. Megido (13 pages).
International Search Report and Written Opinion for International Application No. PCT/US2021/014371, mailed Mar. 22, 2021, by S. Bissmire (14 pages).
International Search Report and Written Opinion for International Application No. PCT/US2022/024806, mailed Jul. 21, 2022, by M. Rodriguez-Palmero (12 pages).
International Search Report and Written Opinion for International Application No. PCT/US2023/078211 dated Feb. 12, 2024, by N. Hick (13 pages).
International Search Report and Written Opinion for International Application No. PCT/US2023/083090, mailed on Apr. 30, 2024, by I. Estanol (12 pages).
Izumi, K. et al., "Current Clinical Trials in Pemphigus and Pemphigoid", Frontiers in Immunology, vol. 10, p. 978 (May 3, 2019).
Jenner, G., "Steric effects in high pressure Knoevenagel reactions," Tetrahedron Lett., 42(2): 243-245 (2001).
Johnson, M., et al., "Coding for Dry Eye," Optometric Management, Issue: Mar. 2004 (1 page).
Jordan, V., "Tamoxifen: A Most Unlikely Pioneering Medicine," Nat Rev. Drug Discov., 2:205-213 (2003).
Ashizawa, K., Crystallization of Pharmaceuticals and Chemistry of Polymorphic Phenomena, pp. 273, 278, 305-317 (2002).

D = Dose ($D_L$ - $D_H$); L= Low; H = High
A = Disso mod($A_F$ - $A_S$); F= Fast; S = Slow
P = Polymer coat ($P_F$ - $P_S$); F= Fast; S = Slow

MODIFIED RELEASE FORMULATIONS OF 2-[3-[4-AMINO-3-(2-FLUORO-4-PHENOXY-PHENYL) PYRAZOLO[3,4-D] PYRIMIDIN-1-YL]PIPERIDINE-1-CARBONYL]-4-METHYL-4-[4-(OXETAN-3-YL) PIPERAZIN-1-YL]PENT-2-ENENITRILE

CROSS-REFERENCE TO RELATED APPLICATIONS

This application is a divisional of U.S. application Ser. No. 17/082,747, filed Oct. 28, 2020, which is a continuation of U.S. application Ser. No. 16/312,258, filed Dec. 20, 2018, which is a national stage entry of International Application No. PCT/US2017/040075, filed on Jun. 29, 2017, which claims the benefit of priority to U.S. Provisional Application No. 62/356,345, filed Jun. 29, 2016, the contents of each of which are incorporated by referenced herein in their entirety.

FIELD OF THE DISCLOSURE

The present disclosure relates to modified release formulations of and methods of administration of a Bruton's tyrosine kinase (BTK) inhibitor.

The Bruton's tyrosine kinase (BTK) inhibitor is Compound (I) as disclosed herein and/or a pharmaceutically acceptable salt thereof. Compound (I) and/or a pharmaceutically acceptable salt thereof is a potent BTK inhibitor and hence can be useful for the treatment of diseases such as cancer, autoimmune diseases, and inflammatory diseases.

BACKGROUND OF THE DISCLOSURE

Therapeutic agents can be administered to patients via several different routes such as oral, topical, intravenous, subcutaneous, inhalation, etc. Oral dosing of therapeutics is by far the most preferred route of administration and offers multiple advantages over other routes of administration. Orally delivered drugs are easily self-administered, thereby resulting in increased patient compliance and obviating the requirement for specialized delivery devices for injectable or inhaled therapies or delivery in a therapeutic setting. Oral administration is typically the safest route of getting a drug into the body since it does not require complicated devices or puncturing of body surfaces or membranes. Additionally, dosage is readily controlled, which can be challenging for other modes of administration such as inhaled therapies.

Despite numerous advantages, obtaining consistent and adequate circulating levels of drug with oral dosing can be challenging due to, among other things: poor aqueous solubility; slow dissolution rate in biological fluids; poor stability of drug at physiological pH; poor permeation through biomembranes; extensive presystemic metabolism; and inadequate or inconsistent systemic absorption between individuals or within specific regions of the gastro-intestinal system. Additionally, drug absorption can vary from therapy to therapy and depends upon numerous factors such as whether the patient is in a fed or fasted state at the time of administration, or whether the drug is taken concurrently with other medications. From a safety standpoint, minimizing the total dosage requirement for efficacy as well as reducing variability in absorption should allow for fewer unwanted side effects. Therefore, specific methods for delivery of an oral medication which allow efficient and consistent exposure of the medication are highly desirable.

Targeted therapy has received increased attention, particularly in the oncology area, due to the clinical success of kinase inhibitors as anti-cancer agents. The ongoing challenges to the development of targeted therapies include achieving high selectivity for the primary target and prolonged inhibition to maximize their therapeutic efficacy. Covalent drugs have become a highly attractive approach to designing next generation targeted therapies due to their enhanced ability to achieve high selectivity as well as prolonged inhibition even with significantly reduced systemic exposure of the drugs. Covalent drugs achieve their high selectivity and exceptional potency due to the covalent interaction with a specific cysteine residue in the active site of proteins to which the drug molecule binds. This covalent binding additionally provides prolonged efficacy with increased duration of action that outlasts the systemic exposure of the drug. Drugs containing an acrylamide moiety as Michael acceptors generally react irreversibly with thiols like glutathione and may also react irreversibly with proteins other than the desired target, especially proteins with hyper-reactive cysteines.

Reversible covalent drug molecules (i.e., drugs which contain a Michael acceptor with a second electron withdrawing group) can exhibit poor bioavailability or delayed systemic absorption when the drug is administered orally, which can be manifested by low plasma area under the curve (AUC) and/or $C_{max}$ values, resulting in suboptimal efficacy in vivo. The poor bioavailability of this new class of drugs can be attributed, in part, to the reactivity of reversible covalent Michael acceptor moieties in these drugs. Accordingly, by limiting the exposure of the reversible covalent drugs to the stomach where the combination of low pH and digestive or metabolic enzymes and other sources of thiols occur, a significant increase in systemic exposure of the drug can be obtained.

In addition, limiting the exposure of irreversible covalent drug molecules to the stomach may also lead to a significant increase in systemic exposure of the drug and a reduction in potential adverse side effects such as diarrhea, nausea, emesis, and dizziness. For example, when ibrutinib, an irreversible covalently bound drug molecule, is administered intraduodenally, the bioavailability unexpectedly increased from 21% to 100% compared to direct oral administration as determined by AUC (D. M. Goldstein, Formulations Comprising Ibrutinib, WO 2014/004707, published Jan. 3, 2014). Gastric bypass of ibrutinib should increase bioavailability and/or reduce or altogether eliminate potential adverse side effects of this drug, such as diarrhea, nausea, emesis, and dizziness.

Furthermore, the expression of metabolizing enzymes, such as cysteine proteases, mucins, transporters, and reactive thiol containing molecules in the stomach, such as glutathione, can also contribute to the low oral bioavailability of reversible covalent Michael acceptor-containing drugs (see, e.g., Johnson D. S., et. al., Future Med Chem. 2010 Jun. 1; 2(6):949-964 and Potashman M. H. et al. J. Med. Chem., Vol 52, No. 5. Pgs. 1231-1246). For example, the combination of digestive enzymes, such as the cysteine protease, pepsin, transporters, and metabolizing enzymes such as CYP enzymes in the gastric mucosa, can result in high chemical and/or metabolic transformation of the reversible and irreversible covalent Michael acceptors at low pH. Accordingly, by avoiding exposure of the reversible covalent drugs to the stomach where the combination of low pH and digestive or metabolic enzymes and other sources of thiols occur, a significant increase in systemic exposure of these drugs can be obtained. Additionally, avoidance of exposure to the stomach may reduce or altogether eliminate potential adverse side effects of these drugs such as diarrhea and emesis, commonly called vomiting.

Accordingly, it would be desirable to have modified release formulations of covalent drug molecules which avoid extensive exposure to the stomach. The present disclosure provides such advantageous formulations.

Compound (I) is a reversible covalent inhibitor of Bruton's tyrosine kinase (BTK), which is a member of the Tec tyrosine kinase family. BTK is expressed in most hematopoietic cells, such as B cells, mast cells, and macrophages, but not in T cells, natural killer cells, and plasma cells. BTK plays a role in the development and activation of B cells. Mutations in the human BTK gene cause the inherited disease X-linked agammaglobulinemia (XLA), with lack of peripheral B cells and low levels of serum Ig. In XLA, the primary immune deficit is B cell specific. The development of drugs which inhibit BTK can have therapeutic significance in the treatment of both B cell-related hematological cancers (e.g., non-Hodgkin lymphoma (NHL) and B cell chronic lymphocytic leukemia (B-CLL)), and autoimmune diseases (e.g., rheumatoid arthritis, Sjogren's syndrome, *Pemphigus*, IBD, lupus, and asthma).

Compound (I), currently in development for treatment of autoimmune diseases, is disclosed in Example 31 of the PCT International Application No. PCT/US2013/058614, filed on Sep. 6, 2013.

PCT International Application No. PCT/US2015/000303, filed on Dec. 23, 2015, refers to site specific administration of Compound (I) and/or a pharmaceutically acceptable salt thereof.

PCT International Application No. PCT/US2015/000515, filed on Dec. 23, 2015, refers to formulations which deliver reversible and irreversible covalent kinase inhibitors into the small intestine and specifically into the ileum and jejunum of the small intestine.

SUMMARY OF THE DISCLOSURE

The present disclosure provides a modified release solid oral dosage form comprising:
(a) a core composition comprising Compound (I) and/or a pharmaceutically acceptable salt thereof;
(b) a sub-coating layer coating the core composition, said sub-coating layer comprising a polyvinyl alcohol and/or hydroxypropyl methyl cellulose; and
(c) an enteric coating layer encapsulating the sub-coating layer and the core composition, said enteric coating layer comprising at least one polymer selected from an acrylic/methacrylic/ethacrylic acid homopolymer and copolymer thereof, a cellulose derivative, and a polyvinylpyrrolidone.

The present disclosure also provides a method of treating a disease mediated by BTK to a subject in need thereof, comprising administering to the subject in need of such treatment the modified release solid oral dosage form of this disclosure.

BRIEF DESCRIPTION OF THE FIGURES

Eight corners of "design space" are shown:
Corner 1-30 mg, fast release core, fast coat;
Corner 2-30 mg, slow release core, fast coat;
Corner 3-30 mg, slow release core, slow coat;
Corner 4-30 mg, fast release core, slow coat;
Corner 5-100 mg, fast release core, slow coat;
Corner 6-100 mg, fast release core, fast coat;
Corner 7-100 mg, slow release core, fast coat;
Corner 8-100 mg, slow release core, slow coat.

DETAILED DESCRIPTION OF THE DISCLOSURE

Definitions

Figure 1:
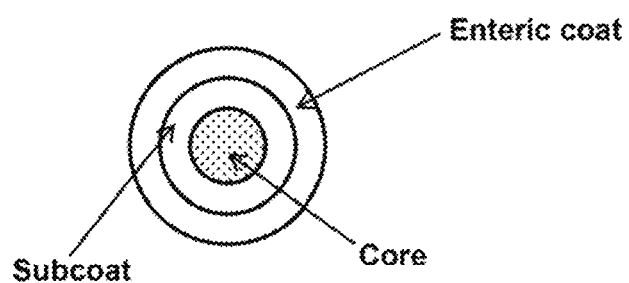
FIG. 1 is a schematic of a modified release solid oral dosage form of this disclosure, comprising the core composition, the sub-coating layer, and the enteric coating layer.

Unless otherwise stated, the following terms used in the specification and claims are defined for the purposes of this Application and have the following meanings. All undefined technical and scientific terms used in this Application have the meaning as commonly understood by one of ordinary skill in the art to which this disclosure belongs.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%.

Compound (I) as used herein means (E) isomer, (Z) isomer, or a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl) piperazin-1-yl]pent-2-enenitrile, or a mixture of (R) and (S) isomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile having the structure:

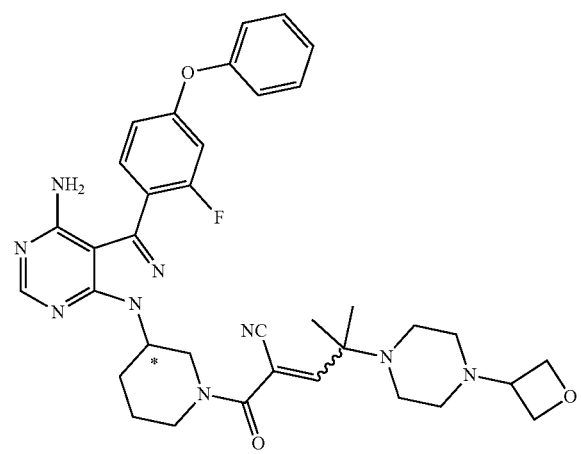 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

where *C is a stereochemical center;
or a pharmaceutically acceptable salt thereof.

It will be understood by a person of ordinary skill in the art that when Compound (I) is denoted as (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, it may contain the corresponding (S) enantiomer as an impurity in less than about 1% by weight. Accordingly, when Compound (I) is denoted as a mixture of (R) and (S) isomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, it means that the amount of (R) or (S) enantiomer in the mixture is greater than about 1% by weight. Similar analysis applies when Compound (I) is denoted as the (E) isomer, (Z) isomer, or a mixture of (E) and (Z) isomers. Compound (I) or a pharmaceutically acceptable salt thereof may also referred to in the specification as "drug", "active agent", or "a therapeutically active agent" or a "API".

"Mammal" as used herein means domesticated animals (such as dogs, cats, and horses), and humans. In one embodiment, a mammal is a human.

A "pharmaceutically acceptable salt" as used herein means an acid addition salt that is pharmaceutically acceptable and that possesses the desired pharmacological activity of the compound from which the salt is made (hereafter, sometimes referred to as "parent compound"). Such salts include salts, formed with inorganic acids such as hydrochloric acid, hydrobromic acid, sulfuric acid, phosphoric acid, and the like; or formed with organic acids such as formic acid, acetic acid, propionic acid, hexanoic acid, lactic acid, malonic acid, succinic acid, malic acid, maleic acid, fumaric acid, tartaric acid, citric acid, benzoic acid, mandelic acid, methanesulfonic acid, ethanesulfonic acid, 1,2-ethanedisulfonic acid, benzenesulfonic acid, 4-toluenesulfonic acid, and the like.

A "pharmaceutically acceptable carrier or excipient" means a carrier or an excipient that is useful in preparing a pharmaceutical composition; is generally safe and neither biologically nor otherwise undesirable, and includes a carrier or an excipient that is acceptable for mammalian pharmaceutical use.

As used herein, "modified-release" as applied to a drug product refers to drug products that alter the timing and/or the rate of release of the drug substance. A modified-release dosage form is a formulation in which the drug-release characteristics of time course and/or location are chosen to accomplish therapeutic or convenience objectives not offered by conventional dosage forms such as solutions, ointments, or promptly dissolving dosage forms. Several types of modified-release oral drug products are recognized. Non-limiting examples include:

1. Extended-release drug products. A dosage form that allows at least about a two-fold reduction in dosage frequency as compared to that drug presented as an immediate-release (conventional) dosage form. Examples of extended-release dosage forms include controlled-release, sustained-release, and long-acting drug products.
2. Delayed-release drug products. A dosage form that releases a discrete portion or portions of drug at a time other than promptly after administration. An initial portion may be released promptly after administration. Enteric-coated dosage forms are common delayed-release products (e.g., enteric-coated aspririn and other NSAID products).
3. Targeted-release drug products. A dosage form that releases drug at or near the intended physiologic site of action. Targeted-release dosage forms may have either immediate- or extended-release characteristics.
4. Orally disintegrating tablets (ODT). ODT have been developed to disintegrate rapidly in the saliva after oral administration. ODT may be used without the addition of water. The drug is dispersed in saliva and swallowed with little or no water.

"Treating" or "treatment" of a disease includes:
(1) inhibiting the disease, i.e., arresting or reducing the development of the disease or its clinical symptoms; or
(2) relieving the disease, i.e., causing regression of the disease or its clinical symptoms.

A "therapeutically effective amount" means the amount of Compound (I) and/or a pharmaceutically acceptable salt thereof that, when administered to a mammal in need or recognized need of treatment for treating a disease, is sufficient to effect such treatment for the disease. The "therapeutically effective amount" will vary depending on the compound, the disease and its severity, and the age, weight, etc., of the mammal to be treated.

"Substantially pure" as used herein refers to a compound (or salt thereof) such as Compound (I) (or salt thereof), wherein at least about 70% by weight of the compound (or salt thereof) is present as the given solid state form. For example, the phrase "amorphous form of a salt of Compound (I) (or a salt thereof) in substantially pure amorphous form" refers to a solid state form of Compound (I) (or a salt thereof), wherein more than about 70% by weight of Compound (I) (or a salt thereof) is an amorphous form with the remaining present in a crystalline form. In one embodiment, such compositions contain at least about 80% by weight of Compound (I) (or a salt thereof) in amorphous form. In another embodiment, at least about 85% by weight of Compound (I) (or a salt thereof) is in amorphous form. In yet another embodiment, at least about 90% by weight of Compound (I) (or a salt thereof) is in amorphous form. In yet another embodiment, at least about 95% by weight of Compound (I) (or a salt thereof) is in amorphous form. In yet another embodiment, at least about 97% by weight or at least about 98% by weight of Compound (I) (or a salt thereof) is in amorphous form. In yet another embodiment, at least about 99% by weight of Compound (I) is in amorphous form. The relative amounts of crystalline and/or amorphous forms in a solid mixture can be determined by methods well-known in the art. For example, X-Ray diffraction provides a convenient and practical means for quantitative determination of the relative amounts of crystalline and/or amorphous forms in a solid mixture. X-Ray diffraction is adaptable to quantitative applications because the intensities of the diffraction peaks of a given compound in a mixture are proportional to the fraction of the corresponding powder in the mixture. Although all salts of Compound (I) are amorphous, if any crystalline form of Compound (I) (or a salt thereof) is present in a mixture, percent composition of crystalline Compound (I) (or a salt thereof) in an unknown composition can be determined. Preferably, the measurements are made on solid powder of Compound (I) (or a salt thereof). The X-Ray powder diffraction patterns of an unknown composition may be compared to known quantitative standards containing pure crystalline forms, if any, of Compound (I) (or a salt thereof) to identify the percent ratio of a particular crystalline form. If an amorphous form is the major fraction of the composition, the amount may be further compared to the total weight of the solid subject to analysis. This is done by comparing the relative intensities of the peaks from the diffraction pattern of the unknown solid powder composition with a calibration curve derived from the X-Ray diffraction patterns of pure known samples. The curve can be calibrated based on the X-Ray powder diffraction pattern for the strongest peak from a pure sample of crystalline forms of Compound (I) (or a salt thereof). The calibration curve may be created in a manner known to those of skill in the art. For example, five or more artificial mixtures of crystalline forms of Compound (I) (or a salt thereof), at different amounts, may be prepared. In a non-limiting example, such mixtures may contain, about 2%, about 5%, about 7%, about 8%, and about 10% of Compound (I) (or a salt thereof) for each crystalline form. Then, X-Ray diffraction patterns are obtained for each artificial mixture using standard X-Ray diffraction techniques. Slight variations in peak positions, if any, may be accounted for by adjusting the location of the peak to be measured. The intensities of the selected characteristic peak(s) for each of the artificial mixtures are then plotted against the known weight percentages of the crystalline form. The resulting plot is a calibration curve that allows determination of the amount of the crystalline forms of Compound (I) (or a salt thereof) in an unknown sample. For the unknown mixture of crystalline and amorphous forms of Compound (I) (or a salt thereof), the intensities of the selected characteristic peak(s) in the mixture, relative to an intensity of this peak in a calibration mixture, may be used to determine the percentage of the given crystalline form in the composition, with the remainder determined to be the amorphous material. The overall crystallinity may be determined as follows:

$$\% \text{ Crystallinity} = (C/A + C - B) \times 100$$

where C is area under crystalline peaks, A is area under amorphous halo, and B is background noise due to air scattering, fluorescence, etc.

"Amorphous form" means a solid which does not possess a distinguishable crystal lattice and the molecular arrangement of molecules lack a long range order characteristic of a crystal. In particular, amorphous denotes a material that does not show a sharp Bragg diffraction peak.

The term "cellulose derivative" or "polysaccharide derivative" refers to a cellulose polymer or polysaccharide wherein at least a portion of the hydroxyls on the saccharide repeat units have been reacted to form an ether or ester linkage. Examples include and are not limited to hydroxyalkyl celluloses, hydroxyalkyl alkylcelluloses, and carboxyalkyl cellulose esters, such as hydroxypropyl methylcelluloses (e.g., hypromelloses or HPMC), hydroxypropylcelluloses (e.g., HPC), and the like.

The term "hydrophilic" for purposes of the present disclosure relates to materials that have affinity toward water.

The term "water soluble" for purposes of the present disclosure relates to materials that dissolve to the extent required, in an aqueous media at a pH of from about 1 to about 8, and is not particularly limited.

The term "water swellable" for purposes of the present disclosure relates to materials that are relatively insoluble in water, but which can absorb water.

EMBODIMENTS

Without limitation, some specific embodiments of the disclosure include:

Embodiment 1: A modified release solid oral dosage form comprising:

(a) a core composition comprising Compound (I) and/or a pharmaceutically acceptable salt thereof as defined hereinbefore;
(b) a sub-coating layer coating the core composition, said sub-coating layer comprising a polyvinyl alcohol or a hydroxypropyl methyl cellulose; and
(c) an enteric coating layer encapsulating the sub-coating layer and the core composition said enteric coating layer comprising at least one polymer selected from an acrylic/methacrylic/ethacrylic acid homopolymer and copolymers thereof, a cellulose derivative, and a polyvinylpyrrolidone.

Embodiment 2: The modified release solid oral dosage form of Embodiment 1, wherein the cellulose derivative is selected from cellulose acetate phthalate, cellulose acetate tritnellitate, methylcellulose, hydroxypropylmethyl cellulose phthalate (HPMCP), hydroxypropylmethyl cellulose succinate (HPMCS), and hydroxypropylmethylcellulose acetate succinate (HPMCAS).

Embodiment 3: The modified release solid oral dosage form of Embodiment 1 or 2, wherein the sub-coating layer (b) comprises a polyvinyl alcohol, and the enteric coating layer (c) comprises a poly (methacrylic acid-co-ethyl acrylate) copolymer.

Embodiment 4: The modified release solid oral dosage form of Embodiment 3, wherein the polyvinyl alcohol is a pigmented polyvinyl alcohol.

In one embodiment, the pigmented polyvinyl alcohol (PVA) is Opadry® II, available from Colorcon. Opadry® II is a high productivity, water soluble, pH independent complete dry powder film coating system containing polymer, plasticizer, and pigment, which allows for immediate disintegration for fast, active release.

In one embodiment, the poly(methacrylic acid-co-ethyl acrylate) that is comprised in the enteric coating layer of this disclosure is EUDRAGIT® L30 D-55 available from Evonik Industries. This polymer is a poly(methacrylic acid-co-ethyl acrylate 1:1 copolymer that is available in the form of a 30% aqueous dispersion. It has a molar mass of approximately 320,000 g/mol and an acid value of about 315 mg KOH/g polymer.

In another embodiment, the poly(methacrylic acid-co-ethyl acrylate) that is comprised in the enteric coating layer of this disclosure is EUDRAGIT® L 100-55, also available from Evonik. It is also a poly(methacrylic acid-co-ethyl acrylate 1:1 copolymer, which is in the form of solid (white powder), and has a molar mass of approximately 320,000 g/mol and an acid value of about 315 mg KOH/g polymer.

Embodiment 5: The modified release solid oral dosage form of any of Embodiments 1-4, wherein the solid oral dosage form releases less than about 10% by weight of Compound (I) and/or a pharmaceutically acceptable salt thereof, in less than about two hours at a pH less than or equal to about 2.0; at least about 80% by weight of Compound (I) and/or a pharmaceutically acceptable salt thereof in about 15 minutes to about two hours at a pH equal to or more than about 6.0; and any unreleased amount of Compound (I) and/or the pharmaceutically acceptable salt thereof is released by the end of about 7.5 hours at a pH equal to or more than about 6.0.

Embodiment 6: The modified release solid oral dosage form of any of Embodiments 1-5, wherein the core composition comprises Compound (I).

Embodiment 7: The modified release solid oral dosage form of any of Embodiments 1-6, wherein Compound (I) is an (E) and (Z) mixture of a mixture of (R) and (S) isomers of 2-[3-[4-amino-3-(2-fluoro-4-phenoxy-phenyl)-pyrazolo

[3,4-d]pyrimidin-1-yl]piperidine-1-carbonyl]-4-methyl-4-[4-(oxetan-3-yl)piperazin-1-yl]pent-2-enenitrile.

Embodiment 8: The modified release solid oral dosage form of any of Embodiments 1-7, wherein Compound (I) is an (E) and (Z) mixture of (R)-2-[3-[4-amino-3-(2-fluoro-4-phenoxy-phenyl)-pyrazolo[3,4-d]pyrimidin-1-yl]piperidine-1-carbonyl]-4-methyl-4-[4-(oxetan-3-yl)piperazin-1-yl]pent-2-enenitrile.

Embodiment 9: The modified release solid oral dosage form of any of Embodiments 1-8, wherein at least about 85% by weight of Compound (I) and/or a pharmaceutically acceptable salt thereof is the (E) isomer.

Embodiment 10: The modified release solid oral dosage form of any of Embodiments 1-9, wherein at least about 90% by weight of Compound (I) and/or a pharmaceutically acceptable salt thereof is the (E) isomer.

Embodiment 11: The modified release solid oral dosage form of any of Embodiments 1-10, wherein Compound (I) and/or a pharmaceutically acceptable salt thereof is a substantially pure amorphous form.

Embodiment 12: The modified release solid oral dosage form of any of Embodiments 1-11, wherein the core composition comprises about 30 mg to about 100 mg of Compound (I) and/or a pharmaceutically acceptable salt thereof.

Embodiment 13: The modified release solid oral dosage form of any of Embodiments 1-12, wherein the core composition further comprises at least one excipient selected from fillers, drug release modifiers (also referred to as "dissolution modifiers" or "dissolution aids"), disintegrants, and lubricants.

Embodiment 14: The modified release solid oral dosage form of Embodiment 13, wherein the filler comprises at least one of a cellulose derivative and a sugar molecule.

Embodiment 15: The modified release solid oral dosage form of Embodiment 14, wherein the cellulose derivative is microcrystalline cellulose.

Embodiment 16: The modified release solid oral dosage form of Embodiment 15, wherein the microcrystalline cellulose is Avicel® PH-101. This material is available from a number of vendors, such as Sigma-Aldrich and FMC Corporation. The particle size of this material is approximately 50 micrometers.

Embodiment 17: The modified release solid oral dosage form of any of Embodiments 14-16, wherein the sugar molecule is mannitol.

Embodiment 18: The modified release solid oral dosage form of Embodiment 17, wherein the mannitol is spray dried mannitol, available as "Pearlitol® 100SD" from a number of vendors, such as Roquette-Pharma, and having a mean particle diameter of about 100 micrometer.

Embodiment 19: The modified release solid oral dosage form of any of Embodiments 13-18, wherein the drug release modifier is hydroxypropyl methyl cellulose (also known as "Hypromellose").

Embodiment 20: The modified release solid oral dosage form of Embodiment 19, wherein the hydroxypropyl methyl cellulose is METHOCEL™ K 100 Premium LV CR. This material is available from The Dow Chemical Company. The letter "K" denotes that it is a hypromellose product; the number "100" that follows the chemistry designation identifies the viscosity of the product, which is about 100 millipascal-seconds (mPa·s), measured at 2% concentration in water at 20° C. "LV" refers to special low-viscosity products, and "CR" denotes a controlled-release grade.

Embodiment 21: The modified release solid oral dosage form of any of Embodiments 13-20, wherein the disintegrant is crosslinked homopolymer of N-vinyl-2-pyrrolidone (crospovidone).

Embodiment 22: The modified release solid oral dosage form of Embodiment 21, wherein the crospovidone is Kollidon™ CL, available from such vendors as BASF.

Embodiment 23: The modified release solid oral dosage form of any of Embodiments 13-22, wherein the lubricant is sodium stearyl fumarate.

Embodiment 24: The modified release solid oral dosage form of any of Embodiments 13-23, comprising by weight of the core composition:
  about 6 to about 20% of Compound (I) and/or a pharmaceutically acceptable salt thereof;
  about 34 to about 72% of microcrystalline cellulose;
  about 5 to about 25% mannitol;
  about 0 to about 20% of hydroxypropyl methyl cellulose;
  about 0.5 to about 1.5% of crosslinked homopolymer of N-vinyl-2-pyrrolidone; and
  about 0.5 to about 1.5% of sodium stearyl fumarate.

Embodiment 25: The modified release solid oral dosage form of any of Embodiments 1-24, wherein the core composition weighs about 83% to about 91% of the total weight of the solid oral dosage form (i.e., weight of core composition+sub-coating layer+enteric coating).

Embodiment 26: The modified release solid oral dosage form of any of Embodiments 1-25, wherein the pigmented polyvinyl alcohol is OPADRY® II.

Embodiment 27: The modified release solid oral dosage form of any of Embodiments 1-26, wherein the sub-coating layer weighs about 2% to about 4% by weight of the solid oral dosage form (i.e., weight of core composition+sub-coating layer+enteric coating).

Embodiment 28: The modified release solid oral dosage form of any of Embodiments 1-27, wherein the poly(methacrylic acid-co-ethyl acrylate) copolymer of the enteric coating layer is EUDRAGIT® L 30 D-55 or EUDRAGIT® L 100-55.

Embodiment 29: The modified release solid oral dosage form of any of Embodiments 1-28, wherein the enteric coating layer further comprises a solubilizer and a plasticizer/anti-tacking agent.

Embodiment 30: The modified release solid oral dosage form of Embodiment 29, wherein the solubilizer is a polyethoxylated sorbitan ester of oleic acid.

Embodiment 31: The modified release solid oral dosage form of Embodiment 29 or 30, wherein the solubilizer is Polysorbate 80 (Tween™ 80), available from such vendors as Sigma-Aldrich. Polysorbate 80 is derived from polyethoxylated sorbitan and oleic acid. The hydrophilic groups in this compound are polyethers, also known as polyoxyethylene groups, which are polymers of ethylene oxide. In the nomenclature of polysorbates, the numeric designation following polysorbate refers to the lipophilic group, in this case the oleic acid. The full chemical names for polysorbate 80 are. Polyoxyethylene (20) sorbitan monooleate and (x)-sorbitan mono-9-octadecenoate poly(oxy-1,2-ethanediyl).

Embodiment 32: The modified release solid oral dosage form of Embodiment 29, wherein the plasticizer/anti-tacking agent is PlasACRYL™ T20, available from such vendors as Emerson Resources and Evonik Industries. PlasACRYL™ T20 is a 20% emulsion of anti-tacking agent and plasticizer that eases the preparation of a robust spray suspension.

Embodiment 33: The modified release solid oral dosage form of any of Embodiments 1-32, wherein the enteric coating layer weighs about 6% to about 20% of the total weight of the solid oral dosage form (i.e., weight of core composition+sub-coating layer+enteric coating).

Embodiment 34: The modified release solid oral dosage form of any of Embodiments 1-33, wherein the enteric coating layer comprises by total weight of the solid oral dosage form (i.e., weight of core composition+sub-coating layer+enteric coating layer):
about 5 to about 16% of EUDRAGIT® L 30 D-55 or EUDRAGIT® L 100-55;
about 1 to about 3% of PlasACRYL™ T20; and
about 0.3 to about 0.8% of Polysorbate 80.

Embodiment 35: The modified release solid oral dosage form of any of Embodiments 1-34, wherein the core composition weighs about 80% to about 91% of the total weight of the solid oral dosage form (i.e., weight of core composition+sub-coating layer+enteric coating).

Embodiment 36: The modified release solid oral dosage form of any of Embodiments 1-35, wherein the sub-coating layer weighs about 2% to about 4% of the total weight of the solid oral dosage form (i.e., weight of core composition+sub-coating layer+enteric coating).

Embodiment 37: A method of inhibiting Bruton's tyrosine kinase (BTK) in a mammal in need thereof comprising administering to the mammal in need of such BTK inhibition a therapeutically effective amount of Compound (I) and/or a pharmaceutically acceptable salt thereof in a modified release solid oral dosage form of any of Embodiments 1-36.

Embodiment 38: A method of treating a disease mediated by BTK in a mammal in need thereof comprising administering to the mammal in need of such disease treatment a therapeutically effective amount of Compound (I) and/or a pharmaceutically acceptable salt thereof in a modified release solid oral dosage form of any of Embodiments 1-36.

Embodiment 39: The method of Embodiment 38, wherein the disease is an autoimmune disease, cancer, or an inflammatory disease.

Embodiment 40: The method of Embodiment 38 or 39, wherein the disease is acute necrotizing hemorrhagic leukoencephalitis, acute disseminated encephalomyelitis, autoimmune inner ear disease (AIED), autoimmune retinopathy, axonal & neuronal neuropathies, chronic inflammatory demyelinating polyneuropathy (CIDP), demyelinating neuropathies, Devic's disease (neuromyelitis optica), experimental allergic encephalomyelitis, giant cell arteritis (temporal arteritis), Guillain-Barre syndrome, Lambert-Eaton syndrome, chronic Meniere's disease, myasthenia gravis, neuromyotonia, opsoclonus-myoclonus syndrome, optic neuritis, paraneoplastic cerebellar degeneration, peripheral neuropathy, perivenous encephalomyelitis, restless legs syndrome, stiff person syndrome, sympathetic ophthalmia, Takayasu's arteritis, temporal arteritis/Giant cell arteritis, transverse myelitis, multiple sclerosis, dysautonomia, age-related macular degeneration (wet and dry), corneal transplantation, encephalitis, meningitis, vasculitis, or systemic lupus erythematosus (SLE).

Embodiment 41: The method of Embodiment 38 or 39, wherein the disease is rheumatoid arthritis, psoriatic arthritis, lupus, uveitis, myasthenia gravis, warm autoimmune hemolytic anemia, Wegener's granulomatosis, Sjogren's disease, Sjogren's dry eye, non-Sjogren's dry eye disease, psoriasis, Pemphigus, urticaria, or asthma.

Embodiment 42: The method of Embodiment 38 or 39, wherein disease is diffuse large B cell lymphoma, follicular lymphoma, chronic lymphocytic lymphoma, chronic lymphocytic leukemia, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis.

Embodiment 43: Diseases that may be treated by the modified release solid oral dosage form of this disclosure include: acute necrotizing hemorrhagic leukoencephalitis, acute disseminated encephalomyelitis, Addison's disease, agammaglobulinemia, alopecia areata, alopecia universalis, amyloidosis, ankylosing spondylitis, anti-GBM/Anti-TBM nephritis, antiphospholipid syndrome (APS), antiphospholipid antibody syndrome, aplastic anemia, arthritis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenia purpura (ATP), autoimmune thyroid disease, autoimmune urticaria, autoimmune hemolytic anemia, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal osteomyelitis (CRMO), Churg-Strauss syndrome, cicatricial pemphigoid/benign mucosal pemphigoid, coeliac disease, Cogan's syndrome, cold agglutinin disease, congenital heart block, coxsackie myocarditis, CREST disease, Crohn's disease, demyelinating neuropathies, dermatitis herpetiformis, dermatomyositis, Devic's disease (neuromyelitis optica), diabetes, discoid lupus, Dressler's syndrome, dry eye, dysautonomia, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's thyroiditis, hemolytic anemia, Henoch-Schonlein purpura, herpes gestationis, hypogammaglobulinemia, idiopathic pulmonary fibrosis, idiopathic thrombocytopeni purpura (ITP), IgA nephropathy, IgG4-related sclerosing disease, immunoregulatory lipoproteins, inclusion body myositis, inflammatory bowel disease, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), lupus including lupus nephritis, lyme disease, chronic, Meniere's disease, microscopic polyangiitis, mixed connective tissue disease (MCTD), mooren's ulcer, Mucha-Habermann disease, mucous membrane pemphigoid, multiple sclerosis, myasthenia gravis, myositis, narcolepsy, neuromyotonia, neutropenia, ocular cicatricial pemphigoid, opsoclonus-myoclonus syndrome, optic neuritis, Ord's thyroiditis, osteoarthritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, pars planitis (peripheral uveitis), Parsonnage-Turner syndrome, peripheral neuropathy, perivenous encephalomyelitis, pernicious anemia, Pemphigus such as Pemphigus vulgaris, Pemphigus foliaceus, POEMS syndrome, polyarteritis nodosa, polymyalgia rheumatica, polymyositis, postmyocardial infarction syndrome, postpericardiotomy syndrome, primary biliary cirrhosis, primary sclerosing cholangitis, primary biliary cirrhosis, progesterone dermatitis, psoriasis, psoriatic arthritis, psoriaticarthritis, pure red cell aplasia, pyoderma gangrenosum, raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, Still's disease, subacute bacterial endocarditis (SBE), Susac's syndrome, sympathetic ophthalmia, Takayasu's arteritis, temporal arteritis/Giant cell arteritis, thrombocytopenia purpura (TTP), Tolosa-Hunt syndrome, transverse myelitis, Type I, II, & III autoimmune polyglandular syndromes, ulcerative colitis, undifferentiated connective tissue disease (UCTD), uveitis, vasculitis, vesiculobullous dermatosis, vitiligo, vulvodynia, and lupus.

Additional diseases include autoimmune disease, e.g., inflammatory bowel disease, arthritis, lupus including Lupus Nephritis, rheumatoid arthritis, psoriatic arthritis, osteoarthritis, Still's disease, juvenile arthritis, diabetes, myasthenia gravis, granulomatosis with polyangiitis, Hashimoto's thyroiditis, Ord's thyroiditis, Graves' disease, Sjogren's syndrome, dry eye (including Sjogren's dry eye and non-Sjogren's dry eye), multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenia purpura, optic neuritis, scleroderma, primary biliary cirrhosis, Reiter's syndrome, Takayasu's arteritis, temporal arteritis, autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, Pemphigus such as Pemphigus vulgaris and/or foliaceus, bullous pemphigoid, age-related macular degeneration (wet and dry), diabetic macular edema, corneal transplantation, abdominal aortic aneurysm, mucous membrane pemphigoid, and vulvodynia.

In another embodiment, the autoimmune disease is lupus, Pemphigus vulgaris, myasthenia gravis, Sjogren's syndrome, dry eye, multiple sclerosis, Wegener's granulomatosis, autoimmune hemolytic anemia, idiopathic thrombocytopenia purpura, Granulomatosis with Polyangiitis, or rheumatoid arthritis.

In another embodiment, the disease is a heteroimmune condition or disease, e.g., graft versus host disease, transplantation, transfusion, anaphylaxis, allergy, type I hypersensitivity, allergic conjunctivitis, allergic rhinitis, or atopic dermatitis. In another embodiment, the disease is atopic dermatitis.

In yet another embodiment, the disease is an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In another embodiment of this aspect, the mammal is suffering from inflammatory skin disease which includes, by way of example, dermatitis, contact dermatitis, eczema, urticaria, Pemphigus such as Pemphigus vulgaris and/or foliaceus, bullous pemphigoid, rosacea, and scarring psoriatic lesions in the skin, joints, or other tissues or organs. In another embodiment, the inflammatory disease is asthma or dermatitis.

In yet another embodiment, the disease is an inflammatory and/or autoimmune disease, including acute inflammatory and/or autoimmune disease, where corticosteroid therapy is used as the first or second line therapy or first or second line maintenance therapy. In one embodiment, the solid oral dosage form of this disclosure is used for the treatment of:

Endocrine Disorders: Primary or secondary adrenocortical insufficiency (hydrocortisone or cortisone is the first choice: synthetic analogs may be used in conjunction with mineralocorticoids where applicable; in infancy mineralocorticoid supplementation is of particular importance); congenital adrenal hyperplasia; nonsuppurative thyroiditis; hypercalcemia associated with cancer.

Rheumatic Disorders: As adjunctive therapy for short-term administration (to tide the patient over an acute episode or exacerbation) in: psoriatic arthritis, rheumatoid arthritis, including juvenile rheumatoid arthritis (selected cases may require low-dose maintenance therapy), ankylosing spondylitis, acute and subacute bursitis, acute nonspecific tenosynovitis, gout, acute gouty arthritis, post-traumatic osteoarthritis, synovitis of osteoarthritis, epicondylitis.

Collagen Diseases: During an exacerbation or as maintenance therapy in selected cases of: systemic lupus erythematosus, systemic dermatomyositis (polymyositis), and acute rheumatic carditis.

Dermatologic Diseases: Pemphigus; bullous dermatitis herpetiformis; severe erythema multiforme (Stevens-Johnson syndrome); exfoliative dermatitis; mycosis fungoides; severe psoriasis; severe seborrheic dermatitis.

Allergic States: Control of severe or incapacitating allergic conditions intractable to adequate trials of conventional treatment: seasonal or perennial allergic rhinitis; bronchial asthma; contact dermatitis; atopic dermatitis; serum sickness; drug hypersensitivity reactions.

Ophthalmic Diseases: Severe acute and chronic allergic and inflammatory processes involving the eye and its adnexa such as: allergic corneal marginal ulcers, herpes zoster ophthalmicus, anterior segment inflammation, diffuse posterior uveitis and choroiditis, sympathetic ophthalmia, allergic conjunctivitis, keratitis, chorioretinitis, optic neuritis, iritis and iridocyclitis.

Respiratory Diseases: Symptomatic sarcoidosis; Loeffler's syndrome not manageable by other means; berylliosis; aspiration pneumonitis, fulminating or disseminated pulmonary tuberculosis when used concurrently with appropriate antituberculous chemotherapy Hematologic Disorders: Idiopathic thrombocytopeniarpura in adults; secondary thrombocytopenia in adults; acquired (autoimmune) hemolytic anemia; erythroblastopenia (RBC anemia); congenital (erythroid) hypoplastic anemia.

Neoplastic Diseases: For palliative management of: leukemias and lymphomas in adults, acute leukemia of childhood.

Edematous States: To induce a diuresis or remission of proteinuria in the nephrotic syndrome, without uremia, of the idiopathic type or that due to lupus erythematosus.

Gastrointestinal Diseases: To tide the patient over a critical period of the disease in: ulcerative colitis, regional enteritis.

Miscellaneous: Tuberculous meningitis with subarachnoid block or impending block when used concurrently with appropriate antituberculous chemotherapy; trichinosis with neurologic or myocardial involvement.

The solid oral dosage forms of this disclosure can be used for the treatment of above listed diseases optionally in combination with a corticosteroid, noncorticosteroidal, immunosuppressive, and/or anti-inflammatory agents. In one embodiment, the immunosuppressive agent is selected from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, and anti-BAFF/BlyS agent (such as belimumab, VAY736, or blisibimod), leflunomide, and teriflunomide. Preferably, the immunosuppressive agent is rituximab, ofatumumab, obinutuzumab, or veltuzumab, or a biosimilar version thereof.

In yet another embodiment the disease to be treated by the solid oral dosage form of this disclosure is a cancer. In one embodiment, the cancer is a B-cell proliferative disorder, e.g., diffuse large B cell lymphoma, follicular lymphoma, chronic lymphocytic lymphoma (CLL), chronic lymphocytic leukemia, chronic myleogenous leukemia, B-cell acute lymphoblastic leukemia (B-ALL), Philadelphia chromosome positive B-ALL, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis.

In yet another embodiment, the disease to be treated by a solid oral dosage form of this disclosure is a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

Where the subject is suffering from or at risk of suffering from an autoimmune disease, an inflammatory disease, or an allergy disease, Compound (I) and/or a pharmaceutically acceptable salt thereof in the present oral dosage form can be used with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with the solid oral dosage form of the present disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel," which is a well-known anti-cancer drug which acts by enhancing and stabilizing microtubule formation, and analogs of Taxol™, such as Taxotere™. Compounds that have the basic taxane skeleton as a common structure feature have also been shown to have the ability to arrest cells in the G2-M phases due to stabilized microtubules and may be useful for treating cancer in combination with the compounds described herein.

Further examples of anti-cancer agents for use in combination with a solid oral dosage form of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a solid oral dosage form of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer agents that can be employed in combination with a solid oral dosage form of this disclosure include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a solid oral dosage form of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), and triazenes (e.g., decarbazine, etc.). Examples of antimetabolites include but are not limited to folic acid analogs (e.g., methotrexate), pyrimidine analogs (e.g., Cytarabine), and purine analogs (e.g., mercaptopurine, thioguanine, pentostatin).

Examples of natural products useful in combination with a solid oral dosage form of this disclosure include but are not limited to *vinca* alkaloids (e.g., vinblastin, vincristine), epipodophyllotoxins (e.g., etoposide), antibiotics (e.g., daunorubicin, doxorubicin, bleomycin), enzymes (e.g., L-asparaginase), and biological response modifiers (e.g., interferon alpha).

Examples of alkylating agents that can be employed in combination with a solid oral dosage form of this disclosure include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), and triazenes (decarbazine, etc.).

Examples of antimetabolites include, but are not limited to folic acid analog (e.g., methotrexate), and pyrimidine analogs (e.g., fluorouracil, floxuridine, Cytarabine), and purine analogs (e.g., mercaptopurine, thioguanine, pentostatin).

Examples of hormones and antagonists useful in combination with a solid oral dosage form of this disclosure include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide).

Examples of anti-cancer agents which act by arresting cells in the G2-M phases due to stabilized microtubules and which can be used in combination with an BTK inhibitor compound of the disclosure include, but are not limited to, the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (*Asta medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (*Asta medica*), D-68144 (*Asta medica*), Diazonamide A, A-293620 (Abbott), NPI-2350 (*nereus*), Taccalonolide A, TUB-245 (Aventis), A-259754 (Abbott), Diozostatin, (–)-Phenylahistin (also known as NSCL-96F037), D-68838 (*Asta medica*), D-68836 (*Asta medica*), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or is at risk of suffering from a thromboembolic disorder (e.g., stroke), the subject can be treated with a solid oral dosage form of the present disclosure in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, and BIBR 1048.

Additional Optional Ingredients of Solid Oral Dosage Forms of the Present Disclosure Hydrophilic Materials:

Suitable hydrophilic materials comprise water soluble or water swellable materials. Examples of such materials include salts, sugars, and polymers such as hydroxyalkyl celluloses, hydroxyalkyl alkylcelluloses, and carboxyalkyl cellulose esters, for example, hydroxypropyl methylcelluloses (hypromelloses or HPMC), hydroxypropylcelluloses (HPC), and combinations comprising one or more of the foregoing materials. Hydroxypropyl methylcelluloses that are hydrophilic in nature and may be used in the present disclosure are sold in different viscosity grades such as those sold under the brand name Methocel™ available from Dow Chemical Co. Examples of hydroxypropyl methylcelluloses of a low viscosity grade include those available under the brand names Methocel E5, Methocel E-15 LV, Methocel E50 LV, Methocel K100 LV and Methocel F50 LV whose 2% by weight aqueous solutions have viscosities of 5 cP, 15 cP, 50 cP, 100 cP, and 50 cP, respectively. Examples of hydroxypropyl methylcelluloses having medium viscosity include those available under the brand names Methocel E4M and Methocel K4M, both of whose 2% by weight aqueous solutions have a viscosity of 4000 cP. Examples of hydroxypropyl methylcellulose polymers having high viscosity include those available under the brand names Methocel K15M and Methocel K100M whose 2% by weight aqueous solutions have viscosities of 15,000 cP and 100,000 cP, respectively. The hydroxypropyl methylcellulose polymers may be present in the pharmaceutical compositions of the present disclosure in amounts from about 0.1% to about 50% by weight.

The hydroxypropylcellulose polymers that may be used in the present disclosure also include, for example, polymers available under the brand name Klucel™, available from Nippon Soda Co. Hydroxypropylcellulose polymers available under the brand names Klucel EF, Klucel LF, Klucel JF and Klucel GF, whose 2% by weight aqueous solutions have viscosities less than 1000 cP, are examples of low viscosity hydrophilic polymers. A hydroxypropylcellulose polymer available under the brand name Klucel ME, whose 2% by weight aqueous solution has a viscosity in the range from 4,000-6,500 cP, is a medium viscosity hydrophilic polymer. Hydroxypropyl cellulose polymers available sold as HPC-SL, HPC-L, and HPC-M, whose 2% by weight aqueous solutions have viscosities of 3-6 cP, 6-10 cP, and 150-400 cP, respectively, are examples of low viscosity hydrophilic polymers, while HPC-H has a viscosity of 1,000-4000 cP and is an example of a medium viscosity hydrophilic polymer. The hydroxypropylcellulose polymers may be present in an amount from about 0.1% to about 50% by weight.

Water swellable materials suitable for making modified release dosage forms are compounds that are able to expand when they are exposed to aqueous fluids, such as gastrointestinal fluids. One or more water swellable compounds may be present in a coating and optionally one or more pharmaceutically acceptable excipients.

Suitable compounds which can be used as water swellable substances include, for example, low-substituted hydroxypropyl celluloses, e.g., L-HPC, cross-linked polyvinylpyrrolidones, e.g., PVP-XL, Kollidone™ CL and Polyplasdone™ XL, sodium carboxymethylcellulose, cross-linked sodium carboxymethylcellulose, e.g., Ac-di-Sol™ and Primellose™, sodium starch glycolate, e.g., Primojel™, sodium carboxymethylcelluloses, e.g., Nymcel™ ZSB10, sodium carboxymethyl starches, e.g., Explotab™, ion-exchange resins, e.g., Dowex™ or Amberlite™ products, microcrystalline cellulose, e.g., Avicel™ products, starches and pregelatinized starches, e.g., Starch 1500™ and Sepistab ST200™, formalin-casein, e.g., Plas-Vita™, and combinations comprising one or more of the foregoing water swellable substances.

In some embodiments, hydrophilic materials include polyalkylene oxides, polysaccharide gums, and crosslinked polyacrylic acids. Suitable polyalkylene oxides, such as linear polymers of unsubstituted ethylene oxide, include Polyox™ products from The Dow Chemical Company, U.S., having molecular weights about 100,000 to about 7,000,000 Da. Other useful polyalkylene oxide polymers are made from propylene oxide or mixtures of ethylene oxide and propylene oxide.

Polysaccharide gums, both natural and modified (semi-synthetic), can be used. Non-limiting examples are dextran, xanthan gum, gellan gum, welan gum, and rhamsan gum.

Crosslinked polyacrylic acids that can be used include those having properties similar to those described above for alkyl-substituted cellulose and polyalkylene oxide polymers. Useful crosslinked polyacrylic acids include those with viscosities about 4,000 to about 40,000 cP (for a 1% aqueous solution at 25° C.). Three specific examples are CARBOPOL™ grades 971 P, 974P, and 934P (sold by The Lubrizol Corporation, Cleveland, Ohio, USA). Further examples are polymers known as WATER LOCK™, which are starch/acrylate/acrylamide copolymers available from Grain Processing Corporation, Muscatine, Iowa, USA.

The hydrophilicity and water swellability of these polymers cause the subcoat to swell in size after oral administration, due to ingress of water. The release rate of an active agent from the subcoat is primarily dependent upon the rate of water inhibition and the rate at which the active agent dissolves and diffuses from the swollen polymer, which in turn is related to the solubility and dissolution rate of the active agent, the active agent particle size, and/or the active agent concentration in the dosage form.

Suitable "hydrophobic" materials are water-insoluble neutral or synthetic waxes, fatty alcohols such as lauryl, myristyl, stearyl, cetyl, or cetostearyl alcohol, fatty acids and derivatives thereof, including fatty acid esters such as such as glyceryl monostearate, glycerol monooleate, acetylated monoglycerides, stearin, palmitin, laurin, myristin, cetyl esters wax, glyceryl palmitostearate, glyceryl behenate, hydrogenated castor oils, cottonseed oils, fatty acid glycerides (mono-, di-, and tri-glycerides), hydrogenated fats, hydrocarbons, normal waxes, stearic acid, stearyl alcohol, materials having hydrocarbon backbones, and combinations comprising one or more of the foregoing materials. Suitable waxes include, but are not limited to, beeswax, Glycowax® (a N,N'-distearoylethyelenediamine, from Lonza), castor wax, carnauba wax, and wax-like substances.

The solid dosage forms described herein comprise an enteric coating, i.e., as an oral dosage form of a pharmaceutical composition as described herein which utilizes an enteric coating to affect the release of the compound in the intestine of the gastrointestinal tract. An "enterically coated" drug or tablet refers to a drug or tablet that is coated with a substance—i.e., with an "enteric coating"—that remains intact in the stomach but dissolves and releases the drug once the intestine (in one embodiment small intestine) is reached. As used herein, "enteric coating" is a material, such as a polymer material or materials which encase the therapeutically active agent either as a dosage form or as particles. Typically, a substantial amount or all of the enteric coating material is dissolved before the therapeutically active agent is released from the dosage form, so as to achieve delayed dissolution of the therapeutically active agent in the intestine. Enteric coatings are discussed, for example, Loyd, V. Allen; Remington: The Science and Practice of Pharmacy, Twenty-first Ed., (Pharmaceutical Press, 2005; and P. J. Tarcha, Polymers for Controlled Drug Delivery, Chapter 3, CRC Press, 1991. Methods for applying enteric coatings to pharmaceutical compositions are well known in the art, and include, for example, methods disclosed in U.S. Patent Publication No. 2006/0045822.

The dosage form may be a compressed or molded or extruded tablet (coated with an enteric coating or uncoated) containing granules, powder, pellets, beads or particles of Compound (I) and/or a pharmaceutically acceptable salt thereof (or any embodiments thereof) optionally admixed with other excipient(s), which are themselves coated with an enteric coating or uncoated provided at least the tablet and/or the granules, powder, pellets, beads or particles of Compound (I) and/or a pharmaceutically acceptable salt thereof is coated. The oral dosage form may also be a capsule containing pellets, beads, or granules of Compound (I) and/or a pharmaceutically acceptable salt thereof (or any embodiments thereof) optionally admixed with other excipient(s). Some examples of coatings that were originally used as enteric coatings are beeswax and glyceryl monostearate; beeswax, shellac and cellulose, cetyl alcohol, and mastic and shellac, as well as shellac and stearic acid (U.S. Pat. No. 2,809,918) and polyvinylacetate and ethyl cellulose (U.S. Pat. No. 3,835,221). More recently, the enteric coatings used are neutral copolymers of polymethacrylic acid esters (Eudragit L30D). (F. W. Goodhart et al, Pharm. Tech., p. 64-71, April, 1984), copolymers of methacrylic acid and methacrylic acid methyl ester (Eudragit S), a neutral copolymer of polymethacrylic acid esters containing metallic stearates (see Mehta et al U.S. Pat. Nos. 4,728,512 and 4,794,001), cellulose acetate succinate, and hypromellose phthalate.

In some embodiments, the polymers described herein are ionic carboxylic polymers. In other embodiments, the polymers and compatible mixtures thereof, and some of their properties, include, but are not limited to:

Shellac: Also called purified lac, it is a refined product obtained from the resinous secretion of an insect. This coating dissolves in media of pH>7;

Acrylic polymers: The performance of acrylic polymers (primarily their solubility in biological fluids) can vary based on the degree and type of substitution. Examples of suitable acrylic polymers include methacrylic acid copolymers and ammonium methacrylate copolymers. The Eudragit series L, S, and RS (manufactured by Rohm Pharma and known as Evonik®) are available as solubilized in organic solvent, aqueous dispersion, or dry powders. The Eudragit series RL, NE, and RS are insoluble in the gastrointestinal tract but are permeable and are used primarily for colonic targeting. The Eudragit series L, L-30D and S are insoluble in stomach and dissolve in the intestine;

Cellulose Derivatives: Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include: cellulose acetate tritnellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (HPMCAS, e.g., AQOAT (Shin Etsu)). The performance can vary based on the degree and type of substitution. For example, HPMCP such as HP-50, HP-55, HP-55S, and HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions.

Poly Vinyl Acetate Phthalate (PVAP): PVAP dissolves in pH>5, and it is much less permeable to water vapor and gastric fluids. Detailed description of above polymers and their pH-dependent solubility can be found at in the article entitled "Enteric coated hard gelatin capsules" by Professor Karl Thoma and Karoline Bechtold at http://pop.www.capsugel.com/media/library/enteric-coated-hard-gelatin-capsules.pdf.

In one embodiment, the enteric coating is made from acrylic acid, methacrylic acid or ethacrylic acid polymers or copolymers, cellulose acetate (and its succinate and phthalate derivatives), hydroxypropyl methyl cellulose phthalate, polyvinyl acetate phthalate, hydroxyethyl ethyl cellulose phthalate, cellulose acetate tetrahydrophtalate, acrylic resin or shellac. In another embodiment the polymer is chosen from cellulose acetate phthalate (CAP; dissolves above pH 6), polyvinyl acetate phthalate (PVAP, disintegrates at pH 5), hydroxypropyl methyl cellulose phthalate (HPMCP, grade HP50 disintegrates at pH 5 and HP50 disintegrates at 5.5), methylacrylic acid copolymers (Eudragit L 100 and L12.5 disintegrate between about 6 and about 7, Eudragit L-30 and L100-55 disintegrate at pH greater than 5.5 and Eudragit S100, S12.5 and FS 30D disintegrate at pH greater than 7).

In some embodiments, the enteric coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, ionic carboxylic acrylic polymers usually will contain about 10% to about 25% by weight of a plasticizer, especially dibutyl phthalate, polyethylene glycol, triethyl citrate, and triacetin.

Conventional coating techniques such as fluid bed or Wurster coaters, or spray or pan coating are employed to apply coatings. The coating thickness must be sufficient to ensure that the oral dosage form remains intact until the desired site of delivery in the intestinal tract is reached. The amount of plasticizer is optimized for each enteric coating layer and the applied amount of said polymer(s), in such a way that the mechanical properties, i.e., flexibility and hardness of the enteric coating layer(s), for instance exemplified as Vickers hardness, are adjusted so that if a tablet is desired the acid resistance of the pellets covered with enteric coating layer(s) does not decrease significantly during compression of pellets into tablets. The amount of plasticizer is usually above about 5% by weight of the enteric coating layer polymer(s). In one embodiment the amount of plasticizer is about 15% to 50% by weight of the enteric coating layer polymer(s). In another embodiment, the amount of plasticizer is about 20% to about 50% by weight of the enteric coating layer polymer(s). The maximum thickness of the applied enteric coating is normally only limited by processing conditions and the desired dissolution profile.

Colorants, surfactants, anti-adhesion agents, antifoaming agents, lubricants (e.g., carnuba wax or PEG) and other additives may be added to the coatings besides plasticizers to solubilize or disperse the coating material, and to improve coating performance and the coated product. To accelerate the dissolution of the enteric coat, a half-thickness, double coat of enteric polymer (for instance, Eudragit L30 D-55) may be applied, and the inner enteric coat may have a buffer up to about pH 6.0 in the presence of about 10% citric acid, followed by a final layer of standard Eudragit L 30 D-55. Applying two layers of enteric coat, each half the thickness of a typical enteric coat, Liu and Basit were able to accelerate enteric coating dissolution compared to a similar coating system applied, unbuffered, as a single layer (Liu, F. and Basit, A. *Journal of Controlled Release.* 147 (2010) 242-245). The intactness of the enteric coating may be measured, for example, by the degradation of the drug within the micropellets. The enteric coated dosage forms or pellets may be tested in dissolution testing first in gastric fluid and separately in intestinal fluid as described in USP to determine its function. Additives such as dispersants, colorants, pigmented polymers (e.g., poly(ethylacrylate, methylmethacrylate), anti-tacking and anti-foaming agents may also be included into the enteric coating layer(s). Other compounds may be added to increase film thickness and to decrease diffusion of acidic gastric juices into the acid susceptible material.

Formulations disclosed herein contain, unless stated otherwise, one or more pharmaceutically acceptable excipient(s) such as binders, surfactants, diluents, buffering agents, antiadherents, glidants, hydrophilic or hydrophobic polymers, retardants, stabilizing agents or stabilizers, disintegrants or superdisintegrants, dispersants, antioxidants, antifoaming agents, fillers, flavors, colorants, lubricants, sorbents, preservatives, plasticizers, or sweeteners, or mixtures thereof, which facilitate processing of the drug molecule (or embodiments thereof disclosed herein) or a pharmaceutically acceptable salt thereof into preparations which can be used pharmaceutically. The pharmaceutically acceptable excipients can be in the coating and/or the core. Any of the well-known techniques and excipients may be used as suitable and as understood in the art, see for example, Remington: The Science and Practice of Pharmacy, Twenty-first Ed., (Pharmaceutical Press, 2005); Liberman, H. A., Lachman, L., and Schwartz, J. B. Eds., Pharmaceutical Dosage Forms, Vol. 1-2 Taylor & Francis 1990; and R. I. Mahato, Ansel's Pharmaceutical Dosage Forms and Drug Delivery Systems, Second Ed. (Taylor & Francis, 2012).

In some embodiments, the formulations may include one or more pH adjusting agents or buffering agents, for example, acids such as acetic, boric, citric, lactic, phosphoric, and hydrochloric acids; bases such as sodium hydroxide, sodium phosphate, sodium borate, sodium citrate, sodium acetate, sodium lactate, and tris-hydroxymethylaminomethane; and buffers such as citrate/dextrose, sodium bicarbonate, ammonium chloride, and the like. Such acids, bases and buffers are included in an amount required to maintain pH of the composition in an acceptable range.

In some embodiments, the formulations may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite, and ammonium sulfate.

In some embodiments, the formulations may also include one or more antifoaming agents to reduce foaming during processing, which can result in coagulation of aqueous dispersions, bubbles in the finished film, or generally impair processing. Exemplary anti-foaming agents include silicon emulsions and sorbitan sesquoleate.

In some embodiments, the formulations may also include one or more antioxidants, such as non-thiol antioxidants, for example, butylated hydroxytoluene (BHT), sodium ascorbate, ascorbic acid, and tocopherol. In certain embodiments, antioxidants enhance chemical stability where required.

In some embodiments, the formulations may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, the formulations may also include one or more binders. Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinyl-pyrrolidone/vinyl acetate copolymer; crosspovidone; povidone; starch; pregelatinized starch; tragacanth, dextrin, maltodextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum mucilage of isapol husks, polyvinylpyrrolidone (e.g., Polyvidone® CL, Kollidon® CL, Polyplasdone® XL-10), larch arabogalactan, Veegum®, polyethylene glycol, polyethylene oxide, waxes, sodium alginate, and the like.

In general, binder levels of about 10% to about 70% are used in powder-filled gelatin capsule formulations. Binder usage level in tablet formulations varies whether direct compression, wet granulation, roller compaction, or usage of other excipients such as fillers which themselves can act as moderate binder. Formulators skilled in art can determine the binder level for the formulations, but binder usage level of up to about 70% in tablet formulations is common.

In some embodiments, the formulations may also include dispersing agents and/or viscosity modulating agents. Dispersing agents and/or viscosity modulating agents include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 20, 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, RPMC K4M, HPMC K15M, and HPMC K100M), carboxymethylcellulose sodium, methylcellulose, triethylcellulose, hydroxyethyl-cellulose, hydroxypropyl-cellulose, hydroxypropylmethylcellulose phthalate, hydroxypropyl-methylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics® F68, F88, and F108, which are block copolymers of ethylene oxide and propylene oxide); and poloxamines (e.g., Tetronic® 908, also known as Poloxamine® 908, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof.

In some embodiments, the formulations may also include one or more "diluents," which refer to chemical compounds that are used to dilute a compound of interest prior to delivery. Diluents can also be used to stabilize compounds because they can provide a more stable environment Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include, e.g., lactose, starch, mannitol, sorbitol, dextrose, microcrystalline cellulose such as Avicel®; dibasic calcium phosphate, dicalcium phosphate dihydrate; tricalcium phosphate; calcium phosphate; anhydrous lactose; spray-dried lactose; pregelatinized starch; compressible sugar, such as Di-Pac® (Amstar); hydroxypropyl-methylcellulose, hydroxypropylmethylcellulose acetate stearate; sucrose-based diluents; confectioner's sugar; monobasic calcium sulfate monohydrate, calcium sulfate dihydrate; calcium lactate trihydrate; dextrates; hydrolyzed cereal solids; amylose; powdered cellulose; calcium carbonate; glycine; kaolin; mannitol, sodium chloride; inositol; bentonite; and the like.

In some embodiments, the formulation may contain surface active agents or surfactants are long chain molecules that can accumulate at hydrophilic/hydrophobic (water/oil) interfaces and lower the surface tension at the interface. As a result they can stabilize an emulsion. In some embodiments, the surfactant may comprise: Tween® (polyoxyethylene sorbate) family of surfactants, Span® (sorbitan long chain carboxylic acid esters) family of surfactants, Pluronic® (ethylene or propylene oxide block copolymers) family of surfactants, Labrasol®, Labrafil® and Labrafac® (each polyglycolyzed glycerides) families of surfactants, sorbitan esters of oleate, stearate, laurate or other long chain carboxylic acids, poloxamers (polyethylene-polypropylene glycol block copolymers or Pluronic®), other sorbitan or sucrose long chain carboxylic acid esters, mono and diglycerides, PEG derivatives of caprylic/capric triglycerides and mixtures thereof or mixture of two or more of the above. In some embodiments the surfactant phase may comprise a mixture of Polyoxyethylene (20) sorbitan monooleate (Tween 80®) and sorbitan monooleate (Span 80®).

In some embodiments, the formulations may also include one or more "disintegrants," which includes both the dissolution and dispersion of the dosage form when contacted with gastrointestinal fluid. "Disintegration agents" or "disintegrants" facilitate the breakup or disintegration of a substance. Examples of disintegration agents include a starch, e.g., a natural starch such as corn starch or potato starch, a pregelatinized starch such as National 1551 or sodium starch glycolate such as Promogel® or Explotab®, a cellulose such as a wood product, methylcrystalline cellulose, e.g., Avicel®, Avicel® PH101, Avicel® PH 102, Avicel® PH105, Elceme® P100, Emcocel®, Vivacel®, and Solka-Floc®, methylcellulose, croscarmellose, or a cross-linked cellulose, such as cross-linked sodium carboxymethyl-cellulose (Ac-Di-Sol®), cross-linked carboxymethyl-cellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some embodiments, the formulations may also include erosion facilitators. "Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

In some embodiments, the formulations may also include one or more filling agents, also referred to herein as fillers, which include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In some embodiments, the formulations may also include one or more flavoring agents and/or "sweeteners," e.g., acacia syrup, acesulfame K, alitame, anise, apple, aspartame, banana, Bavarian cream berry, black currant, butterscotch, calcium citrate, camphor, caramel, cherry, cherry cream chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the formulations may also include one or more lubricants and/or glidants, which are compounds that prevent, reduce, or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG4000) or a methoxypolyethylene glycol such as Carbowax®, sodium oleate, sodium benzoate, glyceryl behenate, polyethylene glycol, magnesium or sodium lauryl sulfate, colloidal silica such as Syloid®, Cab-O-Sil®, a starch such as corn starch, silicone oil, a surfactant, and the like.

In some embodiments, the formulations may also include one or more solubilizers, which include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins for example Captisol®, ethanol, n-butanol, isopropyl alcohol, cholesterol, bile salts, polyethylene glycol 200-600, glycofurol, transcutol, propylene glycol, dimethyl isosorbide, and the like. In one embodiment, the solubilizer is vitamin E TPGS and/or Captisol®.

In some embodiments, the formulations may also include one or more suspending agents, which include compounds such as polyvinylpyrrolidone, e.g., polyvinylpyrrolidone K112, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

In certain embodiments, the formulations may also include one or more surfactants which include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

In certain embodiments, the formulations may also include one or more viscosity enhancing agents which include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol alginates, acacia, chitosans and combinations thereof.

In some embodiments, the formulations may also include one or more wetting agents which include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts, and the like.

It should be appreciated that there is considerable overlap between excipients used in the solid dosage forms described herein. Thus, the above-listed additives should be taken as merely exemplary, and not limiting, of the types of excipients that can be included in solid dosage forms described herein. The types and amounts of such excipient can be readily determined by one skilled in the art, according to the particular properties desired.

EXAMPLES

Example 1

Examples of Composition of the Modified Release Drug Product

Compound (I) tablet is a modified release oral dosage form. The present disclosure employs a "design space" concept to optimize the modified release (MR) performance of the tablet drug product. The "design space" is three dimensional, with varying dose, the percentage of drug release modifier and the polymer coat percentage to control the region of drug release and therefore delay the drug release time.

The design space limits are:
1. Varying dose range from 30 mg (low dose; $D_L$ (D=Dose; L=Low)) to 100 mg (high dose; $D_H$ (H=High));
2. Drug release modifier (Dissolution Aid) to control drug release in the range of 0.5 to 1.5 hours post-gastric emptying. The drug release modifier is Hypromellose K100 Premium LV and will be varied between 0% (Dissomod is $A_F$; F=Fast; No drug release modifier) and 35% (Dissomod is $A_S$; S=Slow; 35% drug release modifier); and
3. Enteric polymer coat (e.g., Eudragit L30 D-55) percentage between 7% ($P_F$; F=Fast) and 16% ($P_S$; S=Slow) to control drug release, post gastric emptying.

Compound (I) tablet can be manufactured as a unit dose selected from within the 'design space'. If higher doses than 100 mg are required, multiple dose units can be administered.

Figure 2:
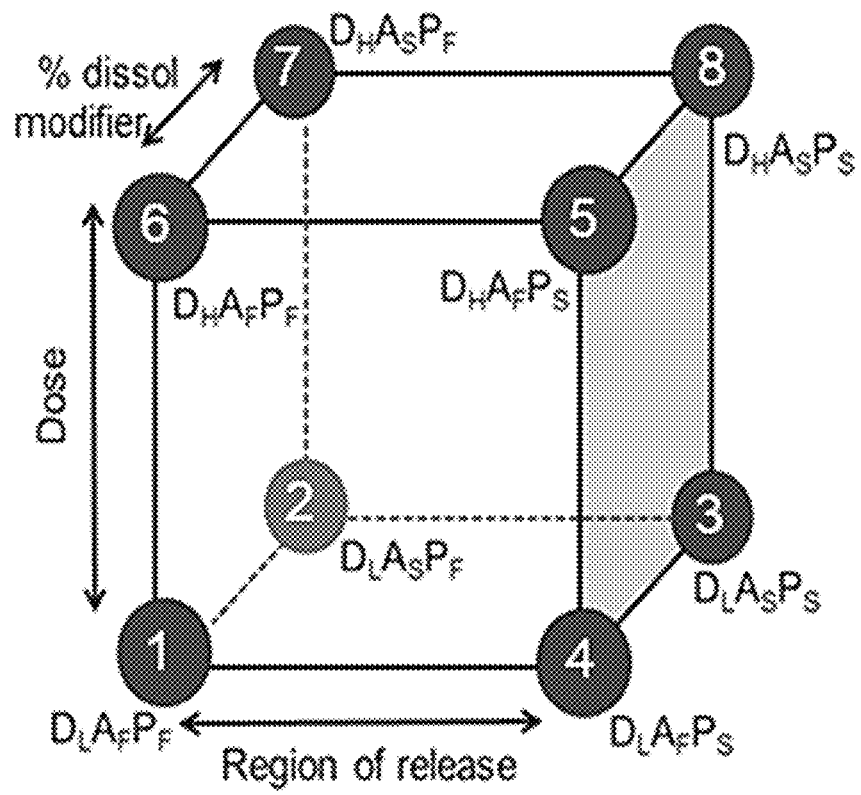
FIG. 2 depicts the "design space" concept to optimize the performance of modified release compositions/formulations of Compound (I). The "design space" is three dimensional, with varying dose, the percentage of drug release modifier, and the polymer coat percentage to control the region of drug release and therefore the drug release delay time.

The design space is shown in FIG. 2.

Under the composition details for the extremes of the "design space" the Compound (I) drug substance mass, Hypromellose K100 Premium LV and Eudragit L30 D55, as shown in Table 1 and 2, can be varied. Any interim formulation within the "design space" can be manufactured. All other components of the formulation will remain constant or adjusted to maintain the weight of the tablet.

TABLE 1

Composition of Compound (I) MR Tablet, Corner 1, 2, 3 and 4

| Component | Quantity per Tablet, (mg) Corner 1 | Quantity per Tablet, (mg) Corner 2 | Quantity per Tablet, (mg) Corner 3 | Quantity per Tablet, (mg) Corner 4 |
|---|---|---|---|---|
| Compound (I) Drug Substance | 30.00 | 30.00 | 30.00 | 30.00 |
| Microcrystalline cellulose PH101 | 347.15 | 172.15 | 172.15 | 347.15 |
| Hypromellose K100 Premium LV | — | 175.00 | 175.00 | — |
| Mannitol (Pearlitol) 100SD | 112.85 | 112.85 | 112.85 | 112.85 |
| Crospovidone CL | 5.00 | 5.00 | 5.00 | 5.00 |
| Sodium Stearyl Fumarate | 5.00 | 5.00 | 5.00 | 5.00 |
| Total Weight of Core Tablet | 500.0 | 500.0 | 500.0 | 500.0 |
| Opadry II yellow | 17.50 | 17.5 | 17.50 | 17.50 |
| Total weight of Sub-Coated Tablet | 517.5 | 517.5 | 517.5 | 517.5 |
| Eudragit L30 D55 | 28.53 | 28.53 | 65.25 | 65.25 |
| PlasACRYL | 5.64 | 5.64 | 12.89 | 12.89 |
| Polysorbate 80 | 2.04 | 2.04 | 4.66 | 4.66 |
| Total weight of Coated Tablet | 553.7 | 553.7 | 600.3 | 600.3 |

Corner 1-Formulation 1 low dose, fast release core, fast coat
Corner 2-Formulation 2 low dose, slow release core, fast coat
Corner 3-Formulation 3 low dose, slow release core, slow coat
Corner 4-Formulation 4 low dose, fast release core, slow coat

TABLE 2

Composition of Compound (I) MR Tablet, Corner 5, 6, 7 and 8

| Component | Quantity per Tablet, (mg) Corner 5 | Quantity per Tablet, (mg) Corner 6 | Quantity per Tablet, (mg) Corner 7 | Quantity per Tablet, (mg) Corner 8 |
|---|---|---|---|---|
| Compound (I) | 100.00 | 100.00 | 100.00 | 100.00 |
| Microcrystalline cellulose PH101 | 347.15 | 347.15 | 172.15 | 172.15 |
| Hypromellose K100 Premium LV | — | — | 175.00 | 175.00 |
| Mannitol (Pearlitol) 100SD | 42.85 | 42.85 | 42.85 | 42.85 |
| Crospovidone CL | 5.00 | 5.00 | 5.00 | 5.00 |
| Sodium Stearyl Fumarate | 5.00 | 5.00 | 5.00 | 5.00 |
| Total Weight of Core Tablet | 500.0 | 500.0 | 500.0 | 500.0 |
| Opadry II yellow | 17.50 | 17.50 | 17.50 | 17.50 |
| Total weight of Sub-Coated Tablet | 517.5 | 517.5 | 517.5 | 517.5 |
| Eudragit L30 D55 | 65.25 | 28.53 | 28.53 | 65.25 |
| PlasAcryl | 12.89 | 5.64 | 5.64 | 12.89 |
| Polysorbate 80 | 4.66 | 2.04 | 2.04 | 4.66 |
| Total weight of Coated Tablet | 600.3 | 553.7 | 553.7 | 600.3 |

Corner 5-Formulation 5 high dose, fast release core, slow coat
Corner 6-Formulation 6 high dose, fast release core, fast coat
Corner 7-Formulation 7 high dose, slow release core, fast coat
Corner 8-Formulation 8 high dose, slow release core, slow coat Example 2

General Procedure for Drug Dissolution and pH Change: The tablet is placed in acid medium (pH 2) and kept therein for two (2) hours. Thereafter phosphate buffer is added, which changes the pH to 6.0. The tablet coating is dissolved at this pH; the tablet breaks down and the drug is released. Prior to the pH change, i.e., in acid media, less than about 10% of the drug is released. Dissolution profiles are obtained using HPLC.

Example 3

Dissolution profile of corner 1 formulation (30 mg, low dose tablet, fast release core, fast coat, $D_L A_F P_F$). It takes approximately 30 minutes to approximately 45 minutes to release about 80% of the drug after pH switch (from pH 2 to pH 6).

Example 4

Dissolution profile of corner 2 formulation (30 mg, low dose tablet, slow release core, fast coat, $D_L A_S P_F$). It takes approximately 1 hour to release about 80% of drug after the pH switch.

Example 5

Dissolution profile of corner 3 formulation (30 mg, low dose tablet, slow release core, slow coat, $D_L A_S P_S$). It takes approximately 1.5 hours to release about 80% of drug after the pH switch.

Example 6

Dissolution profile of corner 4 formulation (30 mg, low dose tablet, fast release core, slow coat, $D_L A_F P_S$). It takes approximately 1.5 hours to release about 80% of drug after the pH switch.

Example 7

Dissolution profile of corner 5 formulation (100 mg, high dose tablet, fast release core, slow coat, $D_HA_FP_S$). It takes approximately 45 minutes to release about 80% of the drug after pH switch.

Example 8

Dissolution profile of corner 6 formulation (100 mg, high dose tablet, fast release core, fast coat, $D_HA_FP_F$). It takes approximately less than 30 minutes to release about 80% of the drug after pH switch.

Example 9

Dissolution profile of corner 7 formulation (100 mg, high dose tablet, slow release core, fast coat, $D_HA_SP_F$). It takes less than 2 hours to release about 80% of drug after the pH switch.

Example 10

Dissolution profile of corner 8 formulation (100 mg, high dose tablet, slow release core, slow coat, $D_HA_SP_S$). It takes approximately 2 hours to release about 80% of drug after the pH switch.

Example 11

Figure 3:
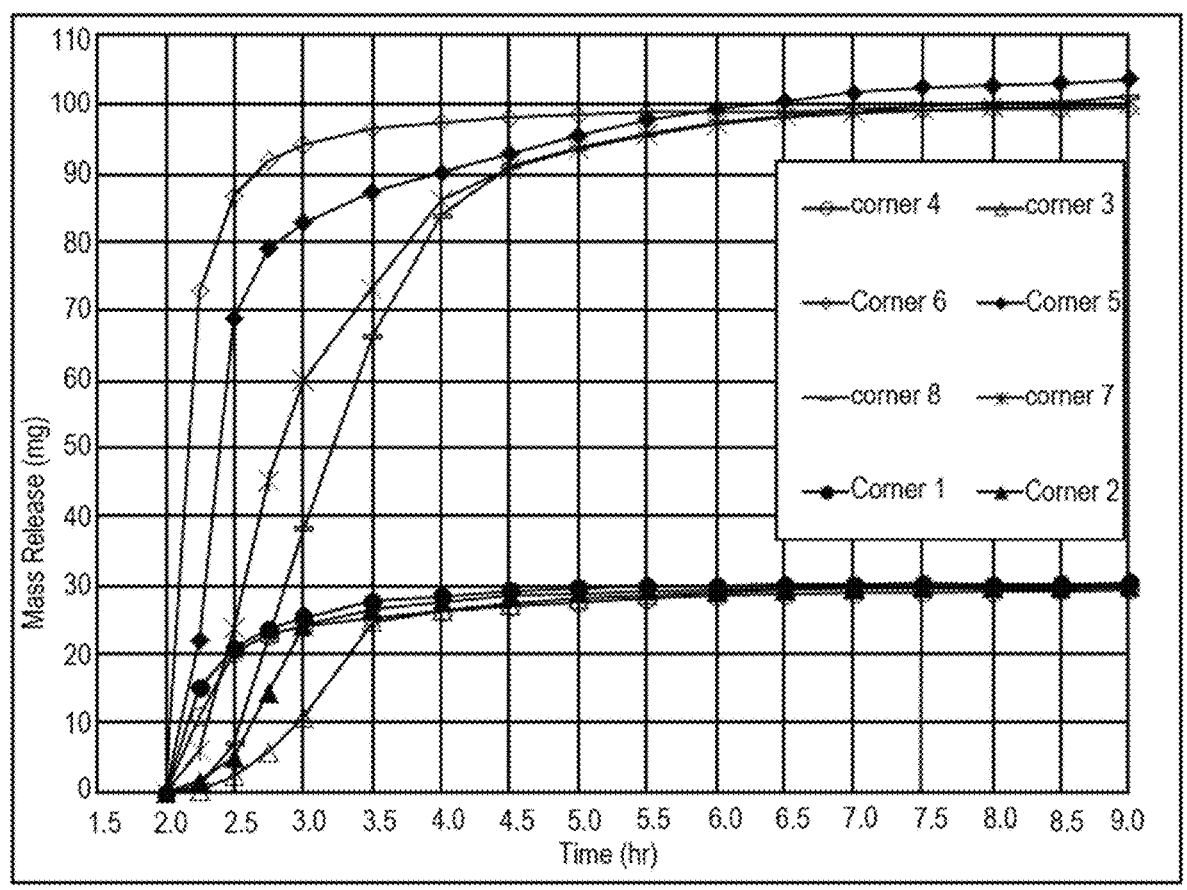
FIG. 3 depicts the dissolution profile of all eight corners of the "design space" in pH 6 dissolution media.

FIG. 3 shows the dissolution profile of all eight corners of the "Design Space" Modified Release Tablet Formulation of Compound (I), which is described in detail in Examples 3-10.

Example 12

Protocol for Preparing the Compound (I) Core Tablet: The Compound (I) drug substance, Microcrystalline Cellulose PH 101, Mannitol 100SD, and Hypromellose K100 Premium LV (if required) are weighted and screened through a suitably sized sieve. The required quantity of each is transferred into a suitably sized blender and mechanically mixed.

The Crospovidone CL is weighed and screened through a suitably sized sieve. The required quantity of Crospovidone is transferred into the above-mentioned suitably sized container.

The sodium stearyl fumarate is weighed and screened through a suitably sized sieve. The required quantity is transferred into the above-mentioned suitably sized container and mechanically mixed. This provides the Compound (I) Modified Release Tablet Blend for compression.

The above-mentioned Compound (I) Modified Release Tablet Blend for compression is individually weighed and transferred into a tablet die for compression using a suitable tablet press. This provides the Compound (I) Modified Release Core Tablet.

This core tablet is placed into a container closure system.

Example 13

Protocol for Preparing the Compound (I) Modified Release Prototype Tablet: The required amount of Opadry II yellow in sterile water is dispersed for irrigation. It is stirred until homogeneous. This provides the Sub-coating Suspension. The sub-coat is applied on the Compound (I) core tablets with the Sub-coating suspension in a perforated coating pan.

The Polysorbate 80 is dissolved in sterile water for irrigation. The Eudragit L30 D-55 and PlasACRYL are dispersed into the Polysorbate solution. The mixture is stirred until homogeneous. This provides the Enteric coating Suspension.

The enteric coat is applied on the sub-coated Compound (I) Modified Release Tablets in the perforated coating pan. The coated tablets are cured. This provides the Enteric coated Compound (I) Modified Release Tablet. All acceptable tablets are placed into the final container closure and labeled.

The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed is:

1. A method of inhibiting Bruton's tyrosine kinase (BTK) in a mammal in need thereof comprising administering to the mammal in need of such BTK inhibition a therapeutically effective amount of a modified release solid oral dosage form comprising:
   (a) a core composition comprising a (E) isomer, a (Z) isomer, a mixture of (E) and (Z) isomers of (R)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, or a mixture of (R) and(S) isomers of 2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile (Compound I) having the structure:

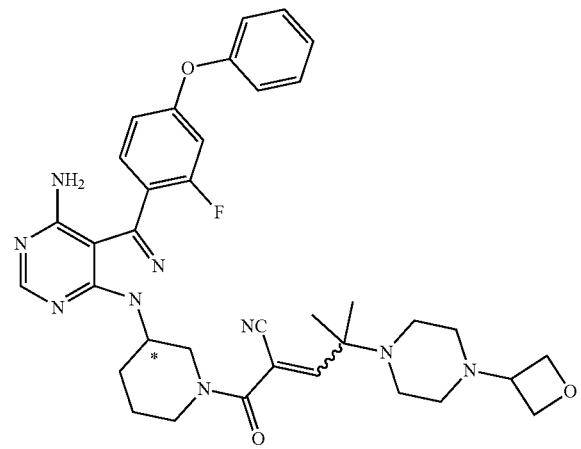 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

where *C is a stereochemical center, or a pharmaceutically acceptable salt thereof; wherein the core composition comprises by weight:

about 6% to about 20% of Compound (I) or a pharmaceutically acceptable salt thereof;
about 34% to about 72% of microcrystalline cellulose;
about 5% to about 25% mannitol;
about 0% to about 20% of hydroxypropyl methyl cellulose;
about 0.5% to about 1.5% of crosslinked homopolymer of N-vinyl-2-pyrrolidone; and
about 0.5% to about 1.5% of sodium stearyl fumarate;
(b) a sub-coating layer coating the core composition, the sub-coating layer comprising a polyvinyl alcohol and/or a hydroxypropyl methyl cellulose; and
(c) an enteric coating layer encapsulating the sub-coating layer and the core composition, the enteric coating layer comprising at least one polymer selected from an acrylic/methacrylic/ethacrylic acid homopolymer and copolymers thereof, a cellulose derivative, and a polyvinylpyrrolidone.

2. A method of treating a disease mediated by Bruton's tyrosine kinase (BTK) in a mammal in need thereof comprising administering to the mammal in need of such disease treatment a therapeutically effective amount of a modified release solid oral dosage form comprising:
(a) a core composition comprising a (E) isomer, a (Z) isomer, a mixture of (E) and (Z) isomers of (R)-2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, (S)-2-3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile, or a mixture of (R) and(S) isomers of 2-[3-[4-amino-3-(2-fluoro-4-phenoxy-phenyl) pyrazolo[3,4-d]pyrimidin-1-yl]piperidine-1-carbonyl]-4-methyl-4-[4-(oxetan-3-yl)piperazin-1-yl]pent-2-enenitrile (Compound I) having the structure:

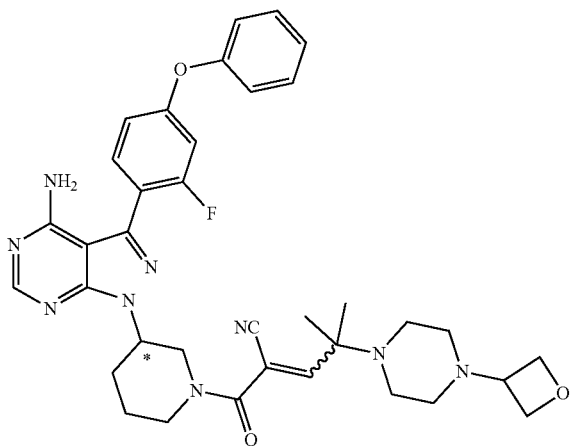 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

where *C is a stereochemical center, or a pharmaceutically acceptable salt thereof; wherein the core composition comprises by weight:
about 6% to about 20% of Compound (I) or a pharmaceutically acceptable salt thereof;
about 34% to about 72% of microcrystalline cellulose;
about 5% to about 25% mannitol;
about 0% to about 20% of hydroxypropyl methyl cellulose;
about 0.5% to about 1.5% of crosslinked homopolymer of N-vinyl-2-pyrrolidone; and
about 0.5% to about 1.5% of sodium stearyl fumarate;
(b) a sub-coating layer coating the core composition, the sub-coating layer comprising a polyvinyl alcohol and/or a hydroxypropyl methyl cellulose; and
(c) an enteric coating layer encapsulating the sub-coating layer and the core composition, the enteric coating layer comprising at least one polymer selected from an acrylic/methacrylic/ethacrylic acid homopolymer and copolymers thereof, a cellulose derivative, and a polyvinylpyrrolidone.

3. The method of claim 2, wherein the disease is an autoimmune disease, an inflammatory disease, or cancer.

4. The method of claim 2, wherein the disease is selected from at least one of acute necrotizing hemorrhagic leukoencephalitis, acute disseminated encephalomyelitis, autoimmune inner ear disease (AIED), autoimmune retinopathy, axonal & neuronal neuropathies, chronic inflammatory demyelinating polyneuropathy (CIDP), demyelinating neuropathies, Devic's disease (neuromyelitis optica), experimental allergic encephalomyelitis, giant cell arteritis (temporal arteritis), Guillain-Barre syndrome, Lambert-Eaton syndrome, chronic Meniere's disease, myasthenia gravis, neuromyotonia, opsoclonus-myoclonus syndrome, optic neuritis, paraneoplastic cerebellar degeneration, peripheral neuropathy, perivenous encephalomyelitis, restless legs syndrome, stiff person syndrome, sympathetic ophthalmia, Takayasu's arteritis, temporal arteritis/Giant cell arteritis, transverse myelitis, multiple sclerosis, dysautonomia, age-related macular degeneration (wet and dry), corneal transplantation, encephalitis, meningitis, vasculitis, and systemic lupus erythematosus (SLE).

5. The method of claim 2, wherein the disease is selected from at least one of rheumatoid arthritis, psoriatic arthritis, lupus, uveitis, myasthenia gravis, warm autoimmune hemolytic anemia, Wegener's granulomatosis, Sjogren's disease, Sjogren's dry eye, non-Sjogren's dry eye disease, psoriasis, pemphigus, urticaria, and asthma.

6. The method of claim 2, wherein the disease is selected from at least one of diffuse large B cell lymphoma, follicular lymphoma, chronic lymphocytic lymphoma, chronic lymphocytic leukemia, B-cell prolymphocytic leukemia, small lymphocytic lymphoma (SLL), multiple myeloma, B-cell non-Hodgkin lymphoma, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, and lymphomatoid granulomatosis.

7. The method of claim 2, wherein the Compound (I) and/or the pharmaceutically acceptable salt thereof is administered in combination with one or more anti-cancer or anti-inflammatory agents.

8. The method of claim 2, wherein the disease is selected from at least one of IgG4-related sclerosing disease, dermatitis, atopic dermatitis, contact dermatitis, idiopathic thrombocytopenia purpura (ITP), autoimmune thrombocytopenia purpura (ATP), thrombocytopenia purpura (TTP), and secondary thrombocytopenia.

9. The method of claim 2, wherein the cellulose derivative is selected from cellulose acetate phthalate, cellulose acetate tritnellitate, methylcellulose, hydroxypropylmethyl cellulose phthalate (HPMCP), hydroxypropylmethyl cellulose succinate (HPMCS), and hydroxypropylmethylcellulose acetate succinate (HPMCAS).

10. The method of claim 2, wherein the sub-coating layer (b) comprises a polyvinyl alcohol, and the enteric coating layer (c) comprises a poly (methacrylic acid-co-ethyl acrylate) copolymer.

11. The method of claim 2, wherein:
the modified release solid oral dosage form releases less than about 10% by weight of Compound (I) or a pharmaceutically acceptable salt thereof in less than two hours at a pH less than or equal to about 2.0;
at least about 80% by weight of Compound (I) or a pharmaceutically acceptable salt thereof in about 15 minutes to about two hours at a pH equal to or more than about 6.0; and
any unreleased amount of Compound (I) is released by the end of about 7.5 hours at a pH equal to or more than about 6.0.

12. The method of claim 2, wherein the core composition comprises Compound (I).

13. The method of claim 2, wherein Compound (I) or a pharmaceutically acceptable salt thereof is an (E) and (Z) mixture of (R)-2-[3-[4-amino-3-(2-fluoro-4-phenoxy-phenyl)-pyrazolo [3,4-d] pyrimidin-1-yl] piperidine-1-carbonyl]-4-methyl-4-[4-(oxetan-3-yl) piperazin-1-yl] pent-2-enenitrile.

14. The method of claim 2, wherein at least about 85% by weight of Compound (I) or a pharmaceutically acceptable salt thereof is the (E) isomer.

15. The method of claim 2, wherein at least about 90% by weight of Compound (I) or a pharmaceutically acceptable salt thereof is the (E) isomer.

16. The method of claim 2, wherein Compound (I) or a pharmaceutically acceptable salt thereof is a substantially pure amorphous form.

17. The method of claim 2, wherein the core composition comprises about 30 mg to about 100 mg of Compound (I) or a pharmaceutically acceptable salt thereof.

18. The method of claim 2, wherein the sub-coating layer weighs about 2% to about 4% by weight of the modified release solid oral dosage form.

19. The method of claim 2, wherein the enteric coating layer weighs about 6% to about 20% of the total weight of the modified release solid oral dosage form.

20. The method of claim 2, wherein the core composition weighs about 80% to about 91% of the total weight of the modified release solid oral dosage form.

* * * * *